United States Patent [19]

Maugh et al.

[11] Patent Number: 5,242,808

[45] Date of Patent: * Sep. 7, 1993

[54] PRODUCTION OF BIOADHESIVE PRECURSOR PROTEIN ANALOGS BY GENETICALLY ENGINEERED ORGANISMS

[75] Inventors: Kathy J. Maugh, Walnut, Calif.; David M. Anderson, Rockville, Md.; Susan L. Strausberg; Robert Strausberg, both of Silver Spring, Md.; Tena Wei, Rockville, Md.

[73] Assignee: Enzon, Inc., Piscataway, N.J.

[ * ] Notice: The portion of the term of this patent subsequent to Sep. 17, 2008 has been disclaimed.

[21] Appl. No.: 644,745

[22] Filed: Jan. 23, 1991

Related U.S. Application Data

[63] Continuation of Ser. No. 25,243, Mar. 12, 1987, abandoned, which is a continuation-in-part of Ser. No. 933,945, Nov. 24, 1986, abandoned, which is a continuation-in-part of Ser. No. 650,128, Sep. 13, 1984, abandoned.

[51] Int. Cl.$^5$ .................. C12P 21/02; C12N 1/19; C12N 1/21; C12N 15/11
[52] U.S. Cl. .................. 435/69.1; 435/69.7; 435/172.3; 435/252.3; 435/252.33; 435/320.1; 435/254.21; 435/254.3; 935/10; 935/60; 935/69; 935/73; 530/353
[58] Field of Search .............. 435/69.1, 69.7, 172.3, 435/320.1, 256, 255, 252.3, 252.33; 530/328, 353; 536/27; 935/10, 11, 23, 28, 29, 69, 73

[56] References Cited

U.S. PATENT DOCUMENTS

| | | | |
|---|---|---|---|
| 4,546,082 | 10/1985 | Kurjan et al. | 435/172.3 |
| 4,585,585 | 4/1986 | Waite | 530/328 |
| 4,687,740 | 8/1987 | Waite | 435/68.1 |
| 4,721,673 | 1/1988 | Uren et al. | 435/183 |
| 5,013,652 | 5/1991 | Strausberg et al. | 435/69.2 |
| 5,049,504 | 9/1991 | Maugh et al. | 435/252.33 |

FOREIGN PATENT DOCUMENTS

| | | |
|---|---|---|
| 1282020 | 3/1991 | Canada . |
| 1085400 | 4/1986 | Japan . |

OTHER PUBLICATIONS

Chen, J. et al., 1985, *EMBO Journal*, vol. 4, No. 9, pp. 2145–2151.
Suggs et al., *PNAS (USA)*, 79(11):6971–6975 (1982).
Waite, J. H., et al., *J. Biol. Chem.*, 258:2911–2915 (1983).
Waite, J. H., In *Mollusca*, vol. 1, pp. 467–504 (1983).
Waite, J. H. and Tanzer, M. L., *Science*, 212:1038–1040 (1981).
Waite, J. H., et al., *Biochem.*, 24:5010–5014 (1985).
Marumo, K. and Waite, J. H., *Biochemica Biophys. Acta*, 872:98–103 (1986).
Skujins, J. J., et al., *Arch. Biochem. Biophys.*, 111:358–364 (1965).
Lerch, K. and Ettlinger, L., *Eur. J. Biochem.*, 31:427–437 (1972).
Waite, J. H., *J. Mar. Biol. Assoc. U.K.*, 65:359–371 (1985).
Gallop, P. M. and Seifter, S., *Meth. Enzymol.*, VI:6-35–641 (1963).
Redl, H. and Schlog, G., *Facial Plastic Surgery*, 2:315–321 (1985).
Waite, J. H., *Biol. Rev.*, 58:209–231 (1983).
Johnson, R., *Gen. Engin. News*, Apr. 1985, pp. 14 & 18.
Waite, J. H., *J. Comp. Physiol. B*, 156:491–496 (1986).
Bowen, H. J., NIDR Symp. on Dental Adhesive Materials, pp. 82–93 (1973).
Lindner, E. et al., *Chem. Abst.*, 87:179439w (1977).

(List continued on next page.)

*Primary Examiner*—Richard A. Schwartz
*Assistant Examiner*—Mary E. Mosher
*Attorney, Agent, or Firm*—Sterne, Kessler, Goldstein & Fox

[57] ABSTRACT

Recombinant production of bioadhesive precursor protein analogs is disclosed. The bioadhesive precursor protein analogs can be hydroxylated and used as an adhesive in wet environments.

37 Claims, 19 Drawing Sheets

OTHER PUBLICATIONS

Lindner, E. et al., *Proc. 3rd Int. Biodegradation Symp.*, (1975), published 1976, J. M. Sharpley et al., eds., Sppl. Dvi. U.K.

Cook, M., in *Adhesion in Biological Systems*, R. S. Manly, ed., Academic Press, N.Y., 1907, pp. 139–150.

Waite, J. H., *Am. Zool.*, 30:126A (1990).

Waite, J. H. et al., *J. Comp. Physiol. B*, 159:517–525 (1989).

Saez, C. et al., *Comp. Biochem. Physiol. B*, 98:569–572 (1991).

Pardo, J. et al., *Prot. Exp. Purif.*, 1:147–150 (1990).

Larson, R., ONR Contract No. N00014–86K–0217.

Waite, Herbert, Annual and Final Report dated Oct. 5, 1988 for ONR Contract No. N00014–86–K0717.

```
                        |  5                    | 10                     |  15
Met Ala Ala |Ala Lys Pro Ser Tyr Pro Pro Thr Tyr Lys |Ala Lys
ATG GCG GCC GCG AAA CCA AGT TAC CCA CCG ACC TAC AAA GCG AAA
─────    ─────────
ClaI      Not I

| 20                    |  25                     30
Pro Ser Tyr Pro Pro Thr Tyr Lys |Ala Lys Pro Ser Tyr Pro Pro
CCA AGT TAC CCA CCG ACC TAC AAA GCG AAA CCG TCT TAC CCA CCG

|  35                     40                     |  45
Thr Tyr Lys |Ala Lys Pro Ser Tyr Pro Pro Thr Tyr Lys |Ala Lys
ACC TAC AAA GCG AAA CCA AGT TAC CCA CCG ACC TAC AAA GCG AAA

|  50                |  55     |           60
Pro Ser Tyr Pro Pro Thr Tyr Lys |Thr Pro Ala |Ala Lys Pro Ser
CCG TCT TAC CCA CCG ACC TAC AAA ACG CCG GCC GCG AAA CCA AGT
                                    ─────────────
                                        Nae I

|  65         |          70                75
Tyr Pro Pro Thr Tyr Lys |Ala Lys Pro Ser Tyr Pro Pro Thr Tyr
TAC CCA CCG ACC TAC AAA GCG AAA CCA AGT TAC CCA CCG ACC TAC

|               80                    85   |                90
Lys |Ala Lys Pro Ser Tyr Pro Pro Thr Tyr Lys |Ala Lys Pro Ser
AAA GCG AAA CCG TCT TAC CCA CCG ACC TAC AAA GCG AAA CCA AGT

95    |          100.                  105
Tyr Pro Pro Thr Tyr Lys |Ala Lys Pro Ser Tyr Pro Pro Thr Tyr
TAC CCA CCG ACC TAC AAA GCG AAA CCG TCT TAC CCA CCG ACC TAC

|             110
Lys |Thr Pro Ala Ser Met
AAA ACG CCG GCA AGC ATC
    ─────────── ───────
        Nae I     Sph I
```

FIG.8

|     |     |     |     |     | 5   |     |     |     |     | 10  |     |     |     |     | 15  |
| --- | --- | --- | --- | --- | --- | --- | --- | --- | --- | --- | --- | --- | --- | --- | --- |
| 1   | Ala | Ala | Ala | Lys | Ppr | Ser | Tyr | Pro | Pro | Thr | Tyr | Lys | Ala | Lys | Pro |
| 16  | Ser | Tyr | Pro | Pro | Thr | Tyr | Lys | Ala | Lys | Pro | Ser | Tyr | Pro | Pro | Thr |
| 31  | Tyr | Lys | Ala | Lys | Pro | Ser | Tyr | Pro | Pro | Thr | Tyr | Lys | Ala | Lys | Pro |
| 46  | Ser | Tyr | Pro | Pro | Thr | Tyr | Lys | Thr | Pro | Ala | Ala | Lys | Pro | Ser | Tyr |
| 61  | Pro | Pro | Thr | Tyr | Lys | Ala | Lys | Pro | Ser | Tyr | Pro | Pro | Thr | Tyr | Lys |
| 76  | Ala | Lys | Pro | Ser | Tyr | Pro | Pro | Thr | Tyr | Lys | Ala | Lys | Pro | Ser | Tyr |
| 91  | Pro | Pro | Thr | Tyr | Lys | Ala | Lys | Pro | Ser | Tyr | Pro | Pro | Thr | Tyr | Lys |
| 106 | Thr | Pro | Ala | Ala | Lys | Pro | Ser | Tyr | Pro | Pro | Thr | Tyr | Lys | Ala | Lys |
| 121 | Pro | Ser | Tyr | Pro | Pro | Thr | Tyr | Lys | Ala | Lys | Pro | Ser | Tyr | Pro | Pro |
| 136 | Thr | Tyr | Lys | Ala | Lys | Pro | Ser | Tyr | Pro | Pro | Thr | Tyr | Lys | Ala | Lys |
| 151 | Pro | Ser | Tyr | Pro | Pro | Thr | Tyr | Lys | Thr | Pro | Ala | Ala | Lys | Pro | Ser |
| 166 | Tyr | Pro | Pro | Thr | Tyr | Lys | Ala | Lys | Pro | Ser | Tyr | Pro | Pro | Thr | Tyr |
| 181 | Lys | Ala | Lys | Pro | Ser | Tyr | Pro | Pro | Thr | Tyr | Lys | Ala | Lys | Pro | Ser |
| 196 | Tyr | Pro | Pro | Thr | Tyr | Lys | Ala | Lys | Pro | Ser | Tyr | Pro | Pro | Thr | Tyr |
| 211 | Lys | Thr | Pro | Ala | Ser | Ser |     |     |     |     |     |     |     |     |     |

*FIG. 9*

```
                          ①10              |15              ②20              |25             ③30
     His Lys Pro Ser Tyr Pro Pro Thr Tyr Lys Pro Thr Tyr Lys Thr Thr Tyr Pro Pro Thr Tyr Lys Ile Ser Tyr Pro
GAA TTC CAT AAA CCA AGT CCA CCA ACT TAT AAA CCT ACA TAT AAA ACA ACT TAT CCT CCA ACT TAT AAA ATA AGT TAT CCT
EcoRI                                                                                                      60
                         ④40              |45              ⑤50              |55              ⑥60
     Pro Thr Tyr Lys Ala Thr Tyr Pro Ser Tyr Pro Ala Thr Tyr Lys Pro Ser Tyr Pro Ala Lys Pro Ser Tyr Pro
     CCA ACT TAT AAA GCA ACT TAT CCA AGT TAT CCA GCA ACT TAT AAA CCA AGT TAT CCA GCA AAA CCA AGT TAT CCT

⑦70              |75              ⑧80              |85              ⑨90
     Pro Thr Tyr Lys Ala Lys Pro Thr Tyr Lys Ala Lys Pro Thr Tyr Lys Ala Lys Pro Thr Tyr Pro Pro Thr Tyr Lys
     CCA ACT TAT AAA GCA AAG CCA ACT TAT AAA GCA AAG CCA ACT TAT AAA GCA AAG CCA ACT TAT CCT CCA ACT TAT AAA

⑩95             |100              ⑪105              |110              ⑫115             |120
     Ala Lys Pro Ser Tyr Pro Pro Thr Tyr Lys Pro Ser Tyr Pro Pro Thr Tyr Lys Ser Lys Ser Ile Tyr Pro Ser Lys
     GCA AAA CCA AGT TAT CCT CCA ACA ACT TAT AAA CCA AGT TAT CCT CCA ACT TAT AAA TCC AAG TCA ATA TAT CCC AAA

⑬125             |130              ⑭135              |140              ⑮145             |150
     Pro Lys Thr Tyr Lys Pro Lys Leu Thr Tyr Pro Lys Tyr Lys Pro Lys Tyr Pro Lys Tyr Pro Lys Ser Tyr Pro Lys
     CCT AAG CCT AAA CTA ACC TAT CCT CAA AAG CCT AAA TAT CCC AAA TAT CCA CCA TCT TAT AAA

⑯155             |160              ⑰165              |170              ⑱175             |180
     Pro Lys Ile Thr Tyr Pro Ser Thr Tyr Lys Leu Lys Pro Ser Tyr Pro Thr Tyr Lys Ser Lys Thr Tyr Pro Thr Asn
     CCT AAG ATT ACT TCA ACT TAT AAA TTG AAG CCA AGT TAT CCT CCA ACA TCT AAA ACA TAC CCT CCT ACA TAT AAC

⑲185             |190              ⑳195              |200             205
     Lys Lys Ile Ser Tyr Pro Ser Ser Tyr Lys Ala Lys Thr Lys Pro Pro Ala Tyr Pro Lys Pro Thr Asn Arg Tyr ***
     AAA AAG ATC AGC TAT CCA TCA TCA TAT AAA GCT AAG ACA AAA CCA CCA GCA TAT CCC ACA AAC AGA TAT TAA TCT CAA TAT TAA
                                                                                                       G     A *
                                                                                                         BclI

AAG TAT TAA CTA AAA TAT TCA CAT TAC TGT ACT ACA CAT TTT AAC GTT TGT ATT GAT GAG GAA CAG ATG AAC ATT TGA TAA TAC ATA

ATC GGG GTT AAT GAT TTG TTA TAT TCA ATC TTA ATA TGT TTG TGA TTT GTT ATG TTC TTG AAG TAT TGT TTC AAA TAA AGT TTA TTC TTT

TCT GGT AAA AAA AAA AAA AAA GGA ATT C
                                   EcoRI
```

```
        5                    10                   15                   20
Tyr Lys Ala Lys Pro Ser Tyr Pro Pro Thr Tyr Lys Ala Lys Pro Thr Tyr Lys Ala Lys
TAT AAA GCA AAA CCA AGT TAT CCT CCA ACT TAT AAA GCA AAG CCA ACT TAT AAA GCA AAG 25                   30                   35                   40
Pro Thr Asn Pro Ser Thr Tyr Lys Ala Lys Pro Ser Tyr Pro Pro Thr Tyr Lys Ala Lys
CCA ACT AAT CCT TCA ACG TAT AAA GCA TAT .AAA CCA AGT TAT CCT CCA ACT TAT .AAA GCA AAA 45                   50                   55                   60
Pro Ser Tyr Pro Pro Thr Tyr Lys Ala Lys Pro Ser Tyr Pro Pro Thr Tyr Lys Ala Lys
CCA AGT TAT CCT CCA ACT TAT AAA GCA AAA CCA AGT TAT CCT CCA ACG TAT AAA GCA AAG 65                   70                   75                   80
Pro Thr Tyr Lys Ala Lys Pro Thr Tyr Pro Ser Thr Tyr Lys Ala Lys Pro Thr Tyr Lys
CCA ACT TAT AAA GCA AAG CCA ACT TAT CCT TCA AGC TAT AAA GCA TAT AAA CCA ACT TAT AAA 85                   90                   95                   100
Ala Lys Pro Thr Tyr Pro Pro Thr Tyr Lys Ala Lys Pro Ser Tyr Pro Pro Thr Tyr Lys
GCA AAG CCA ACT TAT CCT CCA ACT TAT AAA GCA AAA CCA AGT TAT CCT CCA ACA TAT AAA 105                  110                  115                  120
Pro Lys Pro Ser Tyr Pro Pro Thr Tyr Lys Ser Lys Ser Ile Tyr Pro Ser Ser Tyr Lys
CCA AAG CCA AGT TAT CCT CCA ACT TAT AAA TCC AAG TCA ATA TAT CCC TCT TCA TAC AAA

125
Pro Lys Lys Thr Tyr Pro Pro Thr Tyr
CCT AAG AAA ACT TAT CCC CCC ACA TAT
```

FIG. 15

```
        5              10             15          20
Thr Ser Thr Tyr Lys Ala Lys Pre Ser Tyr Pre Pre Thr Tyr Lys Ala Lys Pre Thr Tyr
ACT TCA ACT TAT AAA GCA AAA CCA AGT TAT CCT CCA ACT TAT AAA GCA AAG CCA ACT TAC 25             30             35          40
Pre Ser Thr Tyr Lys Ala Lys Pre Ser Tyr Pre Pre Thr Tyr Lys Pre Lys Ile Ser Tyr
CCT TCA ACG TAT AAA GCA AAA CCA AGT TAT CCT CCA ACT TAT AAA CCT AAG ATA AGT TAT 45             50             55          60
Pre Pre Thr Tyr Lys Ala Lys Pre Ser Tyr Pre Pre Thr Tyr Lys Ala Lys Pre Ser Tyr
CCT CCA ACT TAT AAA GCA AAA CCA AGT TAT CCT CCA ACT TAT AAA GCA AAA CCA AGT TAT 65             70             75          80
Pre Pre Thr Tyr Lys Ala Lys Pre Thr Tyr Lys Ala Lys Pre Thr Asn Pre Ser Thr Tyr
CCT CCA ACT TAT AAA GCA AAG CCA ACT TAT AAA GCA AAG CCA ACT AAT CCT TCA ACG TAT

85
Lys Ala Lys Pre Ser Tyr
AAA GCA AAG CCA AGT TAT
```

FIG. 16

```
ClaI      NotI  5                    10                   15                   20
Ser  Met Ala  Ala Ala Tyr Lys Ile Lys Pro Thr His Pro Ser Thr Tyr Lys Pro Lys Ile
T|CG ATG GC|G GCC GCT TAC AAG ATT AAG CCA ACT CAC CCA TCT ACT TAC AAG CCA AAG ATT 25                   20                   35                   40
Thr Thr Pro Ser Thr Tyr Lys Pro Lys Pro Ser Tyr Pro Pro Thr Tyr Lys Ala Lys Pro
ACT TAC CCA TCT ACT TAC AAG CCA AAG CCA TCT TAC CCA CCA ACT TAC AAG GCT AAG CCA 45                   50                   55                   60
Thr Tyr Lys Pro Lys Ile Thr Tyr Pro Ser Thr Tyr Lys Ile Lys Pro Thr Tyr Pro Ser
ACT TAC AAG CCA AAG ATT ACT TAC CCA TCT ACT TAC AAG ATT AAG CCA ACT TAC CCA TCT 65                   70                   75                   80
Thr Tyr Lys Pro Lys Pro Ser Tyr Pro Pro Thr Tyr Lys Ile Lys Pro Thr Tyr Pro Ser
ACT TAC AAG CCA AAG CCA TCT TAC CCA CCA ACT TAC AAG ATT AAG CCA ACT TAC CCA TCT 85                   90          SphI
Thr Tyr Lys Ala Lys Pro Thr Tyr Lys Gly Thr Ser Met
ACT TAC AAG GCT AAG CCA ACT TAC AAG GGT AC C AGC ATG|C
                                         └──┬──┘
                                         Asp718
```

FIG. 17

```
    ClaI   NotI      5                    10                   15                   20
    Met Ala   Ala Ala Tyr Lys Pro Lys Pro Ser Tyr Pro Pro Thr Tyr Lys Pro Lys Pro Ser
    ICG ATG GC G GCC GCT TAC AAG CCA AAG CCA TCT TAC CCA CCA ACT TAC AAG CCA AAG CCA TCT 25                   30                   35                   40
    Tyr Pro Pro Thr Tyr Lys Pro Lys Pro Ser Tyr Pro Pro Thr Tyr Lys Ile Lys Pro Thr
    TAC CCA CCA ACT TAC AAG CCA AAG CCA TCT TAC CCA CCA ACT TAC AAG ATT AAG CCA ACT 45                   50                   55                   60
    Tyr Pro Ser Thr Tyr Lys Ala Lys Pro Thr Tyr Lys Ile Lys Pro Thr Tyr Pro Ser Thr
    TAC CCA TCT ACT TAC AAG GCT AAG CCA ACT TAC AAG ATT AAG CCA ACT TAC CCA TCT ACT

65 SphI
    Tyr Lys Gly Thr Ser Met
    TAC AAG GGT AC C AGC ATG C
              Asp718
```

FIG. 18

```
ClaI      NotI    5                    10                   15                   20
Ser  Met Ala  Ala Ala Tyr Lys Ile Lys Pro Thr His Pro Ser Thr Tyr Lys Pro Lys Ile
T CG ATG GC G GCC GCT TAC AAG ATT AAG CCA ACT CAC CCA TCT ACT TAC AAG CCA AAG ATT 25                   20                   35                   40
Thr Thr Pro Ser Thr Tyr Lys Pro Lys Pro Ser Tyr Pro Pro Thr Tyr Lys Ala Lys Pro
ACT TAC CCA TCT ACT TAC AAG CCA AAG CCA TCT TAC CCA CCA ACT TAC AAG GCT AAG CCA 45                   50                   55                   60
Thr Tyr Lys Pro Lys Ile Thr Tyr Pro Ser Thr Tyr Lys Ile Lys Pro Thr Tyr Pro Ser
ACT TAC AAG CCA AAG ATT ACT TAC CCA TCT ACT TAC AAG ATT AAG CCA ACT TAC CCA TCT 65                   70                   75                   80
Thr Tyr Lys Pro Lys Pro Ser Tyr Pro Pro Thr Tyr Lys Ile Lys Pro Thr Tyr Pro Ser
ACT TAC AAG CCA AAG CCA TCT TAC CCA CCA ACT TAC AAG ATT AAG CCA ACT TAC CCA TCT 85                   90                   95                  100
Thr Tyr Lys Ala Lys Pro Thr Tyr Lys Gly Thr Lys Ser Tyr Pro Ala Ala Tyr Lys Pro
ACT TAC AAG GCT AAG CCA ACT TAC AAG GGT ACT AAG TCT TAC CCG GCC GCT TAC AAG CCA
                                             *

105                  110                  115                  120
Lys Pro Ser Tyr Pro Pro Thr Tyr Lys Pro Lys Pro Ser Tyr Pro Pro Thr Tyr Lys Pro
AAG CCA TCT TAC CCA CCA ACT TAC AAG CCA AAG CCA TCT TAC CCA CCA ACT TAC AAG CCA 125                  130                  135                  140
Lys Pro Ser Tyr Pro Pro Thr Tyr Lys Ile Lys Pro Thr Tyr Pro Ser Thr Tyr Lys Ala
AAG CCA TCT TAC CCA CCA ACT TAC AAG ATT AAG CCA ACT TAC CCA TCT ACT TAC AAG GCT 145                  150                  155 Asp718      SphI
Lys Pro Thr Tyr Lys Ile Lys Pro Thr Tyr Pro Ser Thr Tyr Lys Gly Thr Ser Met
AAG CCA ACT TAC AAG ATT AAG CCA ACT TAC CCA TCT ACT TAC AAG GGT ACC AGC ATC C
```

FIG.19

PRODUCTION OF BIOADHESIVE PRECURSOR PROTEIN ANALOGS BY GENETICALLY ENGINEERED ORGANISMS

CROSS-REFERENCE TO RELATED APPLICATIONS

This application is a continuation of application Ser. No. 07/025,243, filed Mar. 12, 1987, abandoned, which is a continuation-in-part of application Ser. No. 06/933,945, filed Nov. 24, 1986, abandoned, which is a continuation-in-part of application Ser. No. 06/650,128, filed Sep. 13, 1984, abandoned.

BACKGROUND OF THE INVENTION

1. Field of the Invention

This invention relates to the production of bioadhesives that can be employed to bond substances in wet environments. Typically, the bioadhesives of the invention are employed as marine adhesives, biomedical adhesives or dental adhesives. The invention further relates to the microbial production of bioadhesive precursor proteins that can be converted to bioadhesives by chemical or enzymatic treatment.

BRIEF DESCRIPTION OF BACKGROUND ART

The properties of adhesives generally must be tailored to meet the requirements of the particular environments in which they are to be used. Ideally, an adhesive should be cured and it should maintain both its adhesivity and cohesivity under the conditions of use. Curing is the altering of the physical properties of an adhesive by chemical or enzymatic means. In the case of the bioadhesives produced by the procedures described herein, curing is likely to be due to the cross-linking of adjacent uncured adhesive molecules by catalytic and/or chemical agents. Curing may also involve adhesive cross-linking with the substrate.

Many adhesives that exhibit excellent adhesive properties under dry conditions suffer a substantial or total loss of those properties in wet environments. Furthermore, adhesives of the prior art cannot be cured in wet environments. Consequently, it has been particularly difficult to develop adhesives for use in wet environments, such as marine adhesives or adhesives for use in medical and dental applications.

Marine mussels and other sessile invertebrates have the ability to secrete adhesive substances by which they affix themselves to underwater objects. For example, mussels of the genus *Mytilus.* e.g., the species *Mytilus edulis* and *Mytilus californianus*, deposit an adhesive substance from the mussel foot that becomes cured, forming a permanent attachment to the substrate. A major component of the adhesive deposited by *M. edulis* has been identified as a hydroxylated protein of about 130,000 daltons (Waite, J. H., J. Biol. Chem., 258:2911-2915 (1983)). While this substance might make an excellent adhesive for use in wet environments, isolation of the uncured adhesive from mussels for commercial use is not practical since the extraction of 1 kg of the adhesive substance would be a labor-intensive process requiring about 5 to 10 million mussels.

Biochemical analysis of the *M. edulis* bioadhesive protein has shown it to be rich in lysine (20 residues/100) and hydroxylated amino acids (60 residues/100) (Waite, J. H., supra). At least a portion of the hydroxylated residues are 3,4-dihydroxyphenylalanine (DOPA) and hydroxyproline, formed by post-translational hydroxylation of tyrosine and proline residues, respectively. It is believed that post-translational hydroxylation, particularly of the tyrosine residues, is important in defining the adhesive properties of the protein (Waite, J. H., In Mollusca, Volume I, pp. 467-504 (1983); Pizzi, A., et al., Ind. Eng. Chem. Prod. Res. Dev., 21:309-369 (1982) and Wake, W. C., "Adhesion and the Formulation of Adhesives", Applied Science Publish. Ltd. Barking, England (1982).

U.S. Pat. No. 4,585,585 describes a procedure for preparing a bioadhesive polymer by chemically linking decapeptide units produced by the enzymatic digestion of isolated mussel adhesive protein. In accordance with the disclosure of that patent, a bioadhesive protein is first isolated from phenol glands of mussels of the genus Mytilus using the protein purification procedures described by Waite and Tanzer in *Science.* 212:1038 (1981). The isolated bioadhesive, having a molecular weight of 120,000 to 140,000 daltons, is first treated with collagenase, which reduces its molecular weight by about 10,000 daltons. The treated protein is then digested with trypsin, and the digested protein subjected to gel filtration dialysis to isolate decapeptides of the general formula

NH2-Ala-Lys-Pro/Hyp-Ser/Thr-Tyr/Dopa-Pro/-Hyp-Pro/Hyp-Ser/Thr-Tyr/Dopa-Lys-COOH The decapeptides produced in this manner are then polymerized by the use of chemical linking groups such as glutaraldehyde, oligopeptides, amino acids or other bifunctional linking groups to produce bioadhesives containing up to about 1,000 such decapeptide units.

The procedure of U.S. Pat. No. 4,585,585 still requires the isolation of bioadhesive protein from mussels, which, as previously indicated, is impractical on a commercial scale. Moreover, in addition to the laborious purification procedure, this process adds the additional steps of enzymatic digestion, isolation of the decapeptide fragments and chemical reassemblage of the fragments into a bioadhesive polymer. This arduous procedure is not well-suited to commercial production. Furthermore, analysis of the natural gene described in copending, commonly assigned U.S. patent application Ser. No. 933,945, filed Nov. 24, 1986, demonstrates that there are other significant sequence elements in the mussel adhesive from *Mytilus edulis* besides the sequence specifically claimed. While the repeated decapeptide described is clearly present, it is now known that the 75-80 repeated sequences in the adhesive protein from *M. edulis* contain not only this decapeptide, but other related repeated peptide sequences as well. (Waite, J. H., et al. *Bio. Chem.* 24 5010-5014 (1985) and U.S. patent application Ser. No. 933,945). All of the various repeated peptide sequences are characterized by high concentrations of DOPA and hydroxyproline.

Thus, a need has continued to exist for means and methods for the efficient production of bioadhesives having the excellent properties associated with the mussel foot bioadhesives in wet environments.

A further need has continued to exist for means and methods for producing bioadhesives having the properties of the mussel foot adhesive without the necessity of handling and processing large quantities of mussels.

SUMMARY OF THE INVENTION

This invention involves the production, using techniques of recombinant DNA technology, of bioadhesive precursor proteins which are analogous to the non-hydroxylated polyphenolic adhesive protein produced by marine invertebrates. The invention includes the DNA sequences encoding the bioadhesive precursor protein analogs, the vectors comprising said sequences, hosts transformed with said vectors, the bioadhesive precursor proteins, the hydroxylated bioadhesive proteins and methods of producing the precursor protein, methods of producing the hydroxylated protein, methods of producing adhesives, and methods of using the adhesives.

The bioadhesive precursor protein which is produced by the process of the invention comprises a sequence of from about 50 to about 1500 amino acid residues which comprise from about 20% to 40% proline residues; from about 10% to 40% lysine residues; from about 10% to 40% tyrosine residues; and from 0 to about 40% amino acid residues other than proline, lysine and tyrosine. Preferably, the bioadhesive precursor protein of the invention is comprised of repeating polypeptide sequences. Each polypeptide contains about 20-40% proline residues, 10-40% lysine residues, and 10-40% tyrosine residues and 0-40% of other amino acid residues. Optionally, interspersed throughout are polypeptide linking groups.

The protein produced by the process of the invention can be employed as a bioadhesive precursor. The adhesive properties of the protein are enhanced by hydroxylating at least a portion of the tyrosine residues to 3,4-dihydroxyphenylalanine (DOPA) and, optionally, at least a part of the proline residues to 3- or 4-hydroxyproline by chemical or enzymatic means. The hydroxylated protein is cured to produce the desired physical properties in the bioadhesive. In one embodiment, the hydroxylated bioadhesive precursor protein is analogous to the adhesive protein isolated from the phenol gland of the mussel M. edulis (Waite, J. H., J. Biol. Chem, 258:2911-2915 (1983).

The bioadhesive precursor protein analog is produced by the insertion into an appropriate host, such as E. coli, S. cerevisiae, B. subtilis, A. niger, P. pastorus or mammalian cells of a replicable expression vector containing a chemically synthesized double-stranded DNA (dsDNA) sequence coding for the desired protein and expression of the synthetic dsDNA sequence in the host to yield the protein. The synthetic dsDNA sequence encoding the bioadhesive precursor protein of the invention may be constructed of codons which are selected to optimize expression and provide for stable reproduction of the genetic information in the particular host employed.

The dsDNA sequence encoding the bioadhesive precursor protein can be linked, at its 5' end, to a sequence which encodes an N-terminal portion of a host protein in order to facilitate transcription initiated at a host promoter. In such cases, the expressed protein will constitute a fusion of the bioadhesive precursor protein and the host protein fragment. The host protein fragment may include a signal peptide which, in the case of a host such as S. cerevisiae, facilitates secretion of the expression product across the cell membrane and into the surrounding medium, with attendant cleavage of the signal peptide. Insertion, between the sequences encoding the bioadhesive precursor protein and the host protein fragment, of a dsDNA sequence encoding an amino acid sequence which is specifically cleavable by chemical or enzymatic methods provides a means of cleavage to separate the bioadhesive precursor protein from the host protein fragment.

BRIEF DESCRIPTION OF THE DRAWINGS

FIG. 8 represents the DNA sequence and amino acid sequence of the portion of the tribrid gene of pGX2354 which codes for a 10 repeat decapeptide.

FIG. 9 represents the amino acid sequence of the bioadhesive precursor protein analog encoded by pGX2365, after cyanogen bromide cleavage.

FIG. 13 represents the DNA sequence and translated amino acid sequence for a gene identified as cDNA clone 14-1 which codes for a bioadhesive precursor protein of M. edulis. The asterisk denotes the BclI site introduced by ODM.

Figure 14:
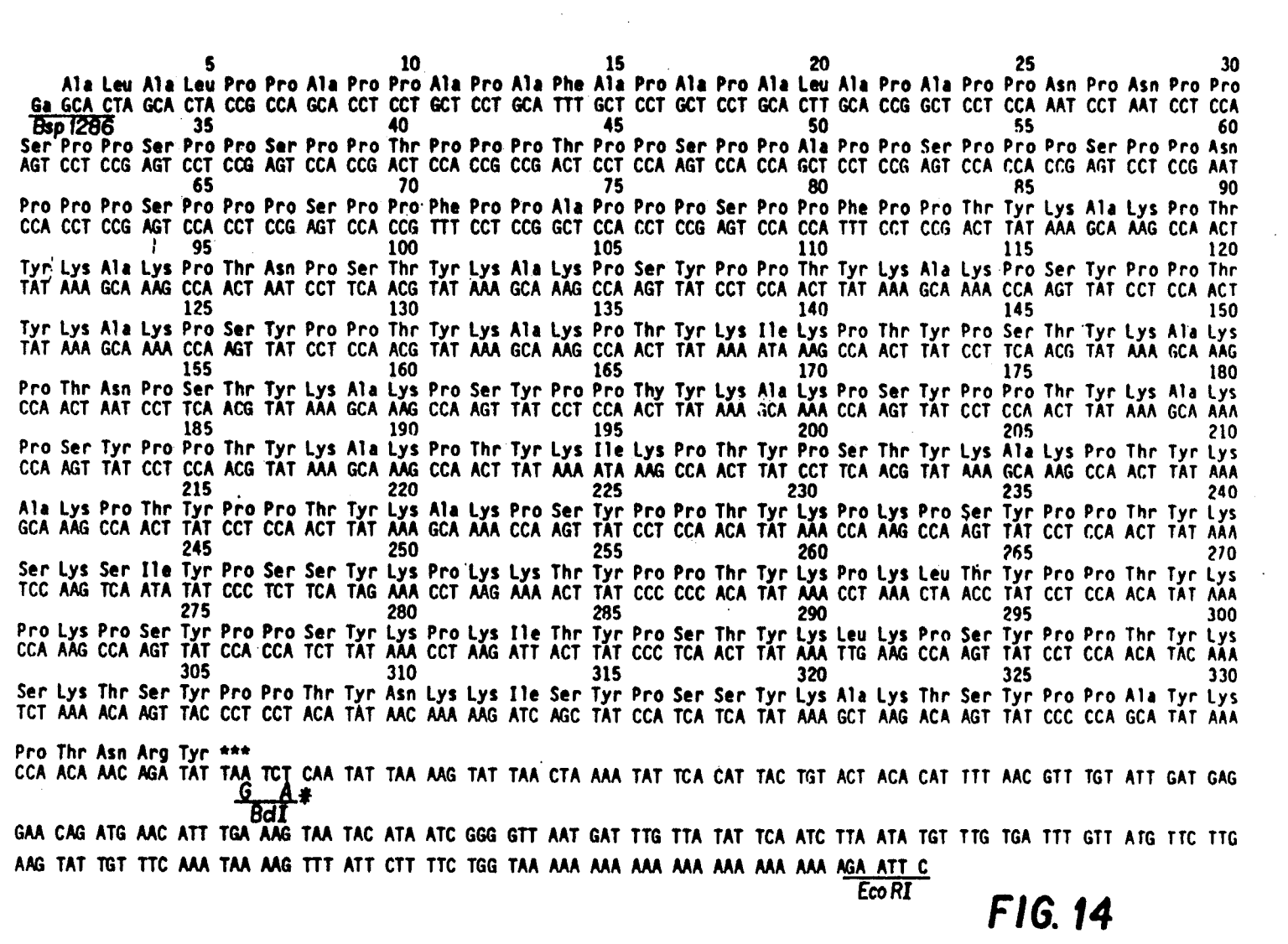

FIG. 14 represents the DNA sequence and translated amino acid sequence for a gene identified as cDNA clone 52, which codes for a bioadhesive precursor protein of M. edulis. The asterisk denotes the BclI site introduced by ODM.

FIG. 15 represents the DNA sequence and translated amino acid sequence for a gene identified as cDNA clone 55, which codes for a bioadhesive precursor protein of *M. edulis.*

FIG. 16 represents the DNA sequence and translated amino acid sequence for a gene identified as cDNA clone 56, which codes for a bioadhesive precursor protein of *M. edulis.*

FIG. 17 represents the DNA sequence of the bioadhesive precursor protein analog gene of plasmid pGX2385 of Example 7, and the amino acid sequence of the bioadhesive precursor protein analog encoded for thereby (ClaI to SphI).

FIG. 18 represents the DNA sequence of the bioadhesive precursor protein analog gene of plasmid pGX2386 of Example 7, and the amino acid sequence of the bioadhesive precursor protein analog encoded for thereby.

FIG. 19 represents the DNA sequence of the bioadhesive precursor protein analog gene of plasmid pGX2393 (ClaI to SphI) of Example 7, and the amino acid sequence of the bioadhesive precursor protein analog encoded for thereby. The asterisk denotes the junction decapeptide which is underlined at the point of joining of the PGX2385 and pGX2386 sequences.

DETAILED DESCRIPTION OF THE INVENTION

Figure 1:
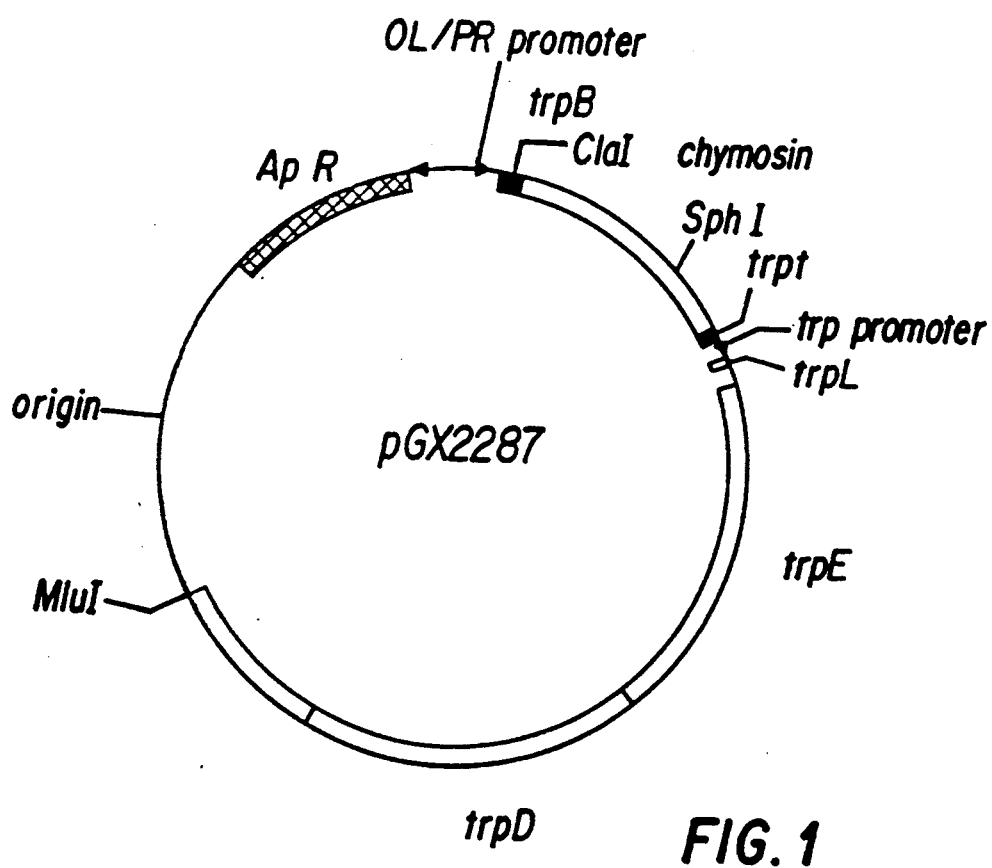
FIG. 1 is a diagram of E. coli plasmid pGX2287, containing the $O_L/P_R$ promoter and encoding a trpB-chymosin fusion protein.

The bioadhesive precursor protein produced by the process of the invention comprises a sequence of from about 50 to about 1500 amino acid residues, preferably from about 600 to about 900 amino acid residues, arranged in repeating polypeptides, preferably repeating decapeptides and hexapeptides. The protein, and preferably each polypeptide, is comprised of about 20% to about 40% proline residues. According to current scientific literature, proline residues impart flexibility to the bioadhesive and render the molecule non-globular, so that the bioadhesive is capable of conforming to the surface of a substrate and interacting with other adhesive molecules. The protein and preferably each polypeptide is also comprised of about 10% to about 40% lysine residues. The lysine residues render the bioadhesive basic, which assists in bonding to underwater surfaces, which are generally coated with a thin film of acidic biological material. It also provides reactive groups through which the protein can be cross-linked during the curing process. The protein and preferably each polypeptide also is comprised of about 10% to about 40% tyrosine residues. The phenolic tyrosine residues provide hydrogen bonding capability to the bioadhesive. Moreover, both the proline and tyrosine residues provide sites for hydroxylation. The addition of a hydroxyl group on the tyrosine to form DOPA is believed to enable the bioadhesive to strongly displace water molecules from the surface of a substrate. In addition to the proline, lysine and tyrosine residues, the protein and preferably each, polypeptide comprises from about 0 to about 40% other amino acid residues. Preferably, these residues, if present, have, non-reactive aliphatic side chains, e.g., alanine, and hydroxyl-containing amino acids, e.g., serine and threonine. These residues are preferably distributed throughout the protein chain so that no more than about four occur together in any given polypeptide sequence. Non-preferred amino acids are acidic amino acids, i.e., aspartic acid and glutamic acid, and cysteine.

The bioadhesive precursor protein analog is produced by inserting a synthetic dsDNA sequence encoding the protein into a replicable expression vector in which it is operably linked to a regulatory sequence that is capable of directing expression of the encoded protein in appropriate host cells. Such host cells, for example, *E. coli* or *S. cerevisiae,* can then be transformed with the expression vector, grown up and subjected to conditions under which the protein is expressed. For purposes of this invention, the term "recombinant protein" is intended to mean a protein produced by a host transformed with a recombinant replicable expression vector.

The dsDNA sequence encoding the bioadhesive precursor protein may be prepared by any of the known methods of DNA synthesis. A suitable method for synthesizing the dsDNA sequence is the phosphite solid-phase method (Tetrahedron Letters, 21:719-722 (1980)). The dsDNA is characterized by the fact that it codes for a protein which is an analog of a naturally occurring adhesive protein which has a repeating structure. By the term "analog" is intended a protein which differs from the naturally occurring protein in its exact amino acid sequence but which includes polypeptide repeating units which are common to a non-posttranslationally modified naturally occurring adhesive protein which has a repeating structure. By the term "bioadhesive precursor protein analog" is intended proteins produced in genetically engineered organisms which comprise repeating polypeptide units which are identical or similar to those found in naturally occurring protein adhesives prior to posttranslational hydroxylation. Particular polypeptide analogs, and the DNA sequences coding for these analogs, are presented in FIGS. 8, 17, 18, and 19.

While the following invention describes in detail bioadhesive precursor protein analogs of the *M. edulis* protein, the invention includes analogs of any and all natural protein adhesives which have a repeating polypeptide structure. For example, the techniques described herein are useful in the development of analog precursors and the hydroxylated derivatives thereof for other protein adhesives from marine invertebrates. Further, as will be recognized by one skilled in the art, the invention further includes bioadhesive precursor protein analog derivatives as well. By the term "bioadhesive precursor protein analog derivative(s)" is intended those polypeptides which differ from the bioadhesive precursor protein analogs by one or more amino acids but which still retain the basic properties of same.

Two basic approaches to synthesize, clone, and express dsDNA sequences encoding a bioadhesive precursor protein analog containing repeats of a single decapeptide sequence were evaluated. The first approach, represented in Examples 1 and 2, was to:

(a) synthesize oligonucleotides encoding one decapeptide repeat;

(b) ligate the oligonucleotides to assemble decapeptide multimer coding sequences;

(c) clone the multimer coding sequences in *E. coli* cloning vectors, using specifically designed linkers to facilitate insertion of the cloned oligonucleotides into the vectors; and (d) transfer the longest cloned sequences into *E. coli* and *S. cerevisiae* expression vectors so that the sequences are expressed as fusion proteins in these respective microbial hosts.

This approach was used to assemble synthetic DNA sequences encoding the polypeptide (ala-lys-pro-ser-tyr-pro-pro-thr-tyr-lys)$_N$ where N indicates the number of direct repeats of this decapeptide sequence. This decapeptide is a component of the polyphenolic adhesive protein of *M. edulis* and was identified in tryptic digests of the natural protein (U.S. Pat. No. 4,585,585). This approach could also be used to assemble synthetic DNA sequences encoding repeats of other polypeptides.

The inventors anticipated that a cloned multimer coding sequence containing for example, 20 repeats of a 10-codon sequence might be unstable in *E. coli*. In order to limit the number of direct DNA repeats in the *E. coli* plasmids, five different oligonucleotides were synthesized, using different codon combinations. However, use of one particular oligonucleotide (GCG AAA CCA AGT TAC CCA CCG ACC TAC AAA) encoding the decapeptide resulted in the most efficient assembly of the multimer coding sequence, and the resulting repetitive DNA sequence was found to be stable in *E. coli*.

For cloning in *S. cerevisiae*, one oligonucleotide, the sequence set out in Example 2, was synthesized containing codons found primarily in genes efficiently translated in yeast.

DNA sequencing and/or restriction enzyme analysis of clones obtained by this approach indicated that DNA fragments encoding up to nine decapeptide repeats had been cloned in *E. coli* and up to three decapeptide repeats had been cloned in *S. cerevisiae*. However, many of the clones had errors in the DNA sequences, causing incorrect codons, frame shifts or termination codons. Therefore, an improved approach for generating a homogeneous 20-decapeptide repeat coding sequence was developed.

The second approach, represented in Example 4, was to:

(a) synthesize oligonucleotides encoding one decapeptide;

(b) ligate the oligonucleotides to assemble decapeptide multimer coding sequences;

(c) clone the multimer coding sequences in *E. coli* expression vectors, using specifically designed 5' and 3' linkers to facilitate insertion of the oligonucleotides and to provide unique restriction sites at the ends of the cloned sequence; and (d) expand the cloned decapeptide coding sequence repeats in the *E. coli* expression vectors using the unique restriction sites at the 5' and 3' ends. (The repeating decapeptide coding sequences can also be transferred to *S. cerevisiae* expression vectors for production of the protein in *S. cerevisiae*).

The synthetic dsDNA encoding the bioadhesive precursor protein analog is inserted into either the *E. coli* or *S. cerevisiae* expression vectors under the control of a regulatory sequence containing a promoter, ribosome binding site and translation initiation signal capable of effecting expression in the selected host.

The expression vector can be selected from plasmids and phages, with plasmids generally being preferred. In order to facilitate expression, the synthetic dsDNA encoding the protein may be linked, at its 5' end, to a sequence encoding an N-terminal portion of the microbial protein which is normally under the control of the particular regulatory sequence employed. For expression in *S. cerevisiae*, the 5' end preceding the sequence encoding the bioadhesive precursor protein analog may also encode a signal peptide for a normally secreted protein which should allow the bioadhesive protein precursor analog to be secreted.

In order to limit the problem of sequence deletion caused by homologous recombination in *E. coli*, the recA *E. coli* host GX3015 was utilized. The synthetic DNA was cloned directly into a derivative of an expression vector (pGX2287, see FIG. 1) previously developed for the production of bovine chymosin (fully described in U.S. Pat. No. 4,798,791 and deposited with the USDA Northern Regional Research Laboratory, Peoria, Illinois with accession No. NRRL-B15788) such that tribrid fusion genes were produced. The genes contain a 5' segment of the highly expressed trpB gene to promote efficient translation initiation, followed by the synthetic bioadhesive precursor protein analog gene, and a 3' region encoding the 159 carboxy terminal amino acids of bovine chymosin. Methionine codons are located on either end of the bioadhesive precursor protein segment so that cyanogen bromide cleavage can be used to release the bioadhesive precursor protein analog from the tribrid fusion protein. Additionally, the plasmid contains a synthetic trpt sequence 3' of the gene to stabilize the mRNA and the trpED genes that effectively stabilize the plasmids in the GX3015 deltatrpED102 host when media without tryptophan is utilized. The promoter is a hybrid lambda OL/PR promoter (fully described in co-pending, commonly assigned U.S. patent application No. 534,982) that is regulated by the temperature-sensitive cI857 repressor produced by a defective lambda lysogen in the GX3015 host. Other specific vector constructions for the expression of the bioadhesive precursor protein analogs will be apparent to those skilled in the art based on the description herein. As a general rule, however, it is advantageous to construct the vector by inserting the bioadhesive precursor protein coding region as an in-frame fusion with another gene that is under the control of an efficient promoter. Preferably, the fusion is constructed such that the encoded fusion protein contains a methionine residue at the 5' end of the bioadhesive precursor protein segment. The recovered bioadhesive precursor protein can thus be treated with cyanogen bromide, using conditions well-known in the art, to remove extraneous amino acid sequences. As those skilled in the art are aware, cyanogen bromide cleaves proteins at methionine residues. Since there are no internal methionine residues within the bioadhesive precursor protein itself, this protein remains intact.

Figure 2:
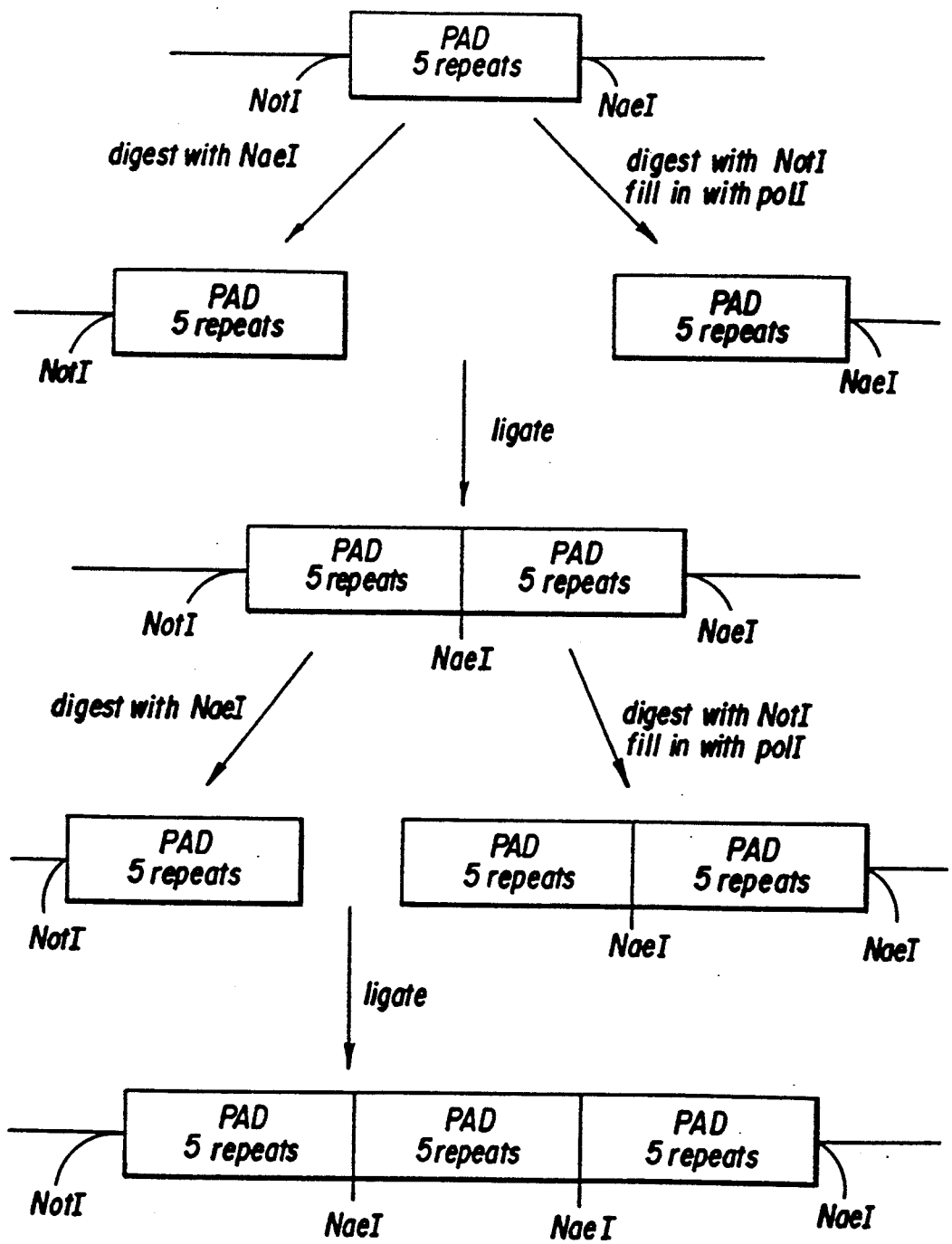
FIG. 2 is a flow chart describing the assembly of a repetitive DNA sequence encoding a bioadhesive precursor protein analog (PAD:polyphenolic adhesive decapeptide).

To assemble DNA sequences encoding repeats of the decapeptide ala-lys-pro-ser-tyr-pro-pro-thr-tyr-lys, oligonucleotides were synthesized that encode the decapeptide sequence and 5' and 3' linker sequences that provide unique restriction sites. These oligonucleotides were annealed and ligated with an *E. coli* expression vector to generate pGX2346, a plasmid that contains three decapeptide coding repeats. The 5' linker encodes a NotI site and the 3' linker encodes a NaeI site. The 5'-end of the pGX2346 decapeptide coding sequence generated by NotI digestion and treatment with DNA polymerase I to fill in the overhang was ligated to the blunt 3' end of the decapeptide coding sequence generated by digesting a second aliquot of pGX2346 with NaeI (see FIG. 2). This creates an in-frame fusion through a linker region that codes for thr-pro-ala. The 5', 3' and internal linkers all code for amino acids (ala, thr, pro, ser) that are found in the prototype decapeptide and thus do not disrupt the general characteristics of the translation products. NotI and NaeI sites were chosen for the linkers because they are unique sites in the plasmids and therefore, simplify the ligations to increase the synthetic gene length. For example, a plasmid with a five decapeptide repeat gene (pGX2348) was doubled to a ten repeat gene (pGX2354) with the thr-pro-ala linker between two five decapeptide repeat genes by simply ligating NotI/DNA polymerase I treated pGX2348 DNA with another aliquot of pGX2348 DNA digested with NaeI, followed by digestion with PvuI (a site in the bla gene of pGX2348) and ligation again at low DNA concentration to favor recircularization of the plasmid. Using this method of multiplying the repeats by ligating NotI/DNA polymerase I treated plasmid DNA to another sample of plasmid cut with NaeI, synthetic genes encoding fifteen (pGX2358) and twenty (pGX2365) repeats were also constructed. The bioadhesive precursor protein analogs encoded by plasmids pGX2348, pGX2354, pGX2358 and pGX2365 have the general sequence shown below flanked by other amino acids at the N- and C-termini:

(ala-lys-pro-ser-tyr-pro-pro-thr-tyr-lys)5-thr-pro-ala]$_n$

While the decapeptide ala-lys-pro-ser-tyr-pro-pro-thr-tyr-lys is repeated many times in the polyphenolic adhesive protein of M. edulis, examination of cDNA sequences encoding portions of this protein (see U.S. patent application Ser. No. 933,945) reveals that many other repetitive decapeptide and hexapeptide sequences are also present in the protein, and that these other sequences may constitute the majority of amino acid sequence of the polyphenolic adhesive protein of M. edulis. For example, in cDNA clone 14-1 nineteen decapeptides and one hexapeptide are encoded (FIG. 13). The decapeptide observed by Waite is encoded in this sequence, but many other decapeptides are also encoded. This heterogeneity in the natural protein sequence indicates that a family of bioadhesive precursor protein analogs could be produced that are related to the natural polyphenolic protein but differ in the frequency of certain decapeptides and hexapeptides and the molecular weight of the protein. This may allow novel adhesive proteins to be specifically designed for a given application. Therefore, in another embodiment, the general approach described above was used to assemble synthetic genes encoding bioadhesive precursor protein analogs composed of several different decapeptide and hexapeptide sequences and of various molecular weights (see Example 7).

Examples of decapaptides and hexapaptides that may be used include PKPSYPPSYK, PKTTYPPTYK, PKISYPPTYK, AKPSYPATYK, AKPSYPPTYK, AKPTYPPTYK, PKPSYPPTYK, SKSIYPSSYK, PKKTYPPTYK, PKLTYPPTYK, PKITYPSTYK, LKPSYPPTYK, SKTSYPPTYN, KKISYPSSYK, AKTSYPPAYK, AKPTYPSTYK, AKPTNPSTYK, AKPSYPSTYK, AKSSYPPTYK, AKTNYPPVYK, PKMTYPPTYK, PKITYPPTYK, PKASYPPTYK, TKKTYPPTYK, AKPSYPPSYK, AKPTYPPSYK, AKPTYK, SKPTYK, and VKPTYK.

It will be readily apparent that modifications can be made in the vector construction such that the expression vector can carry the entire coding region for the bioadhesive precursor protein analog or a coding region for a fragment thereof. Preferably, the fragment contains at least enough of the coding sequence to code for 100 amino acids corresponding to the bioadhesive precursor protein analog.

The expression vector containing the inserted dsDNA coding for the bioadhesive precursor protein is used to transform a host by known techniques of transformation. The expression vector provided by the invention is used to transform any suitable host microorganism, using known means, to produce a transformant. Suitable host organisms include, for example, E. coli or other related gram-negative organisms such as Salmonella. Klebsiella. Erwinia, etc.

Figure 3:
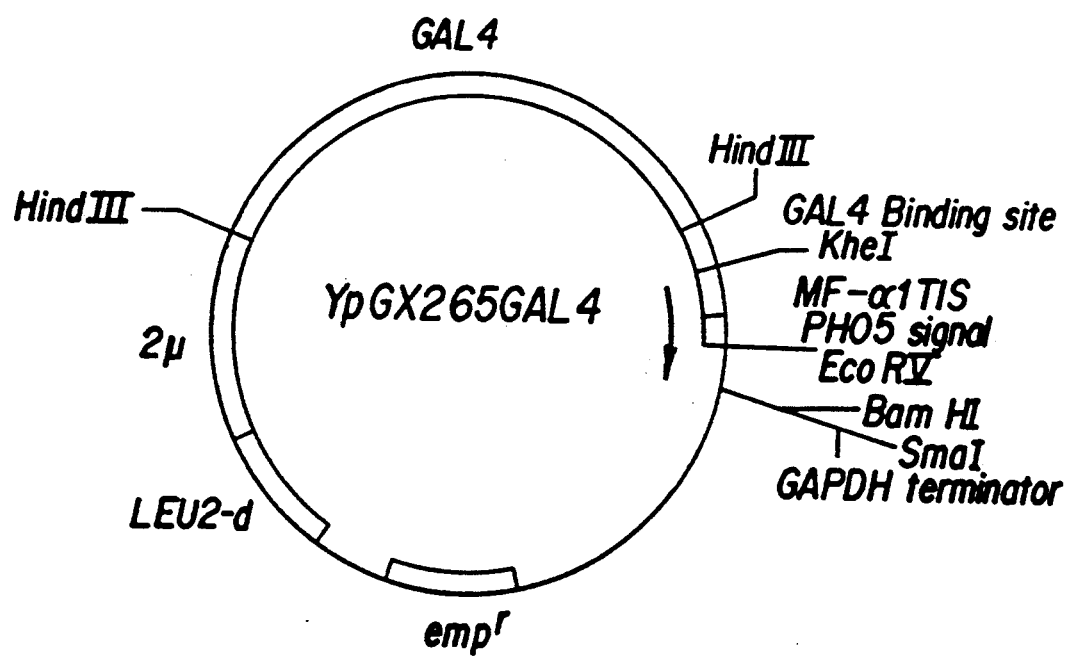
FIG. 3 is a diagram of plasmid YpGX265GAL4, containing a hybrid GAL1/MF-alpha1 promoter, a PHO5 signal coding sequence, a GAPDH transcription terminator, and selectable markers and replication origins for S. cerevisiae and E. coli (TIS: transcription initiation site). BamHI, EcoRV, XhoI and SmaI sites are not unique in the plasmid.

In a different embodiment, the assembled DNA sequence encoding the bioadhesive precursor protein analog may be inserted into an expression vector that functions in a yeast such as Saccharomyces cerevisiae. Typical vectors of this type are disclosed in U.S. Pat. No. 5,013,652, having the title "Composite Yeast Vectors," incorporated by reference herein. One preferred vector for expression of bioadhesive precursor protein analogs in yeast comprises the yeast shuttle vector YpGX265GAL4 (ATCC #67233) (FIG. 3). This vector is characterized by a promoter that is a hybrid derived from the S. cerevisiae GAL1 and MF-aloha 1(alpha-factor) promoters. This promoter system permits galactose-regulated expression. The regulatory gene comprises the GAL4 gene which encodes the GAL4 protein, a positive regulator of the GAL1-MF-alpha1 hybrid promoter. The terminator in the YpGX265GAL4 vector system is derived from synthetic DNA and is based on the S. cerevisiae GAPDH transcription terminator. The signal encoding sequence, also derived from synthetic DNA, is based on the S. cerevisiae PH05 signal. Codons are designed substantially for usage preference in S. cerevisiae.

The YpGX265GAL4 vector contains the LEU2 gene, a marker for plasmid selection in S. cerevisiae. It also contains DNA derived from S. cerevisiae 2-micron plasmid which provides a plasmid replication origin for S. cerevisiae. The vector is further characterized by the E. coli replication origin derived from pJBD207, and an E. coli selectable marker which is ampicillin resistance, also derived from pJBD207.

In a typical vector construction the yeast expression module including the GAL1/MF-alpha1 hybrid promoter and PH05 signal encoding sequence are removed from vector YpGX265GAL4 as a single restriction fragment by digestion with restriction endonucleases HindIII and BamHI and this fragment is ligated with M13mp which has also been digested with HindIII and BamHI. The bioadhesive precursor analog protein coding sequence is removed from an E. coli expression vector such as pGX2365 by restriction endonuclease digestion and is positioned in the M13 vector carrying the yeast expression module so that an in-frame fusion is generated between the yeast signal and bioadhesive precursor protein analog coding sequences. Generation of the desired fusion coding sequence may involve the use of oligonucleotide linkers and/or oligonucleotide-directed mutagenesis. The yeast expression module-fusion protein coding sequence is then excised from the M13 based vector and inserted in the yeast expression vector YpGX265 so that the yeast glyceraldehyde-3-phosphate dehydrogenase transcription terminator is situated downstream from the end of the fusion protein coding region. This vector includes replication origins and selectable markers for plasmid maintenance for both yeast and E. coli. In a final step the yeast GAL4 gene is added to the expression vector as a HindIII restriction fragment.

While the above typifies one construction technique for yeast expression, it is readily apparent that one with ordinary skill can impart modifications and variations within the general teaching. As with the vectors described above, the expression vector may comprise the entire coding region for the bioadhesive precursor protein analog or coding regions for fragments thereof.

Saccharomyces strains carrying mutations in the LEU2 structural gene (e.g., D8 or AH22 (ATCC #38626)) may be transformed with this plasmid, utilizing standard methods. The resulting yeast strain may be grown in an appropriate medium (YNBD, containing 0.7% yeast nitrogen base, 2% glucose, and appropriate nutritional supplements) to maintain the plasmid. For production of the bioadhesive precursor protein, the transformed yeast strain may be grown in an appropriate medium. One suitable medium contains 1% yeast extract, 2% peptone, 1% glucose, and 1% galactose.

The transformant microorganism (*E. coli* or yeast) is cultured under conditions suitable for growth and expression of the bioadhesive precursor protein analog gene. After the protein has been expressed, it is recovered from the transformant cells by known methods such as mechanical or chemical lysis of the cells. The protein can be purified using procedures known in the art, including well-known chromatographic procedures. The bioadhesive precursor protein analog is preferably purified to homogeneity or near homogeneity. In the case of a fusion protein, the recovered protein can be subjected to cyanogen bromide cleavage to remove extraneous peptide sequences.

The recovered bioadhesive precursor protein analog is converted to a bioadhesive by hydroxylation. In particular, it is likely to be necessary to hydroxylate at least a portion of the tyrosine residues, and optionally a portion of the proline residues, an event that occurs in vivo in the marine animal. Hydroxylation converts tyrosine residues to DOPA residues and, optionally a portion of the proline residues to hydroxyproline residues. The DOPA hydroxyl groups are believed to displace water at the bond surfaces, thus contributing to the excellent wet strength of the adhesive, and DOPA residues oxidized to quinones participate in intermolecular cross-linking which cures the adhesive and imparts cohesivity.

Any suitable chemical or enzymatic means for effecting hydroxylation can be employed. It is preferred, however, to effect hydroxylation enzymatically using an enzyme such as mushroom tyrosinase or *Streptomyces antibioticus* tyrosinase. Enzymatic hydroxylation procedures using these enzymes are carried out as generally described by Ito et al., *Biochem. J.* 222:407–411 (1984) and Marumo and Waite, *Biochem. Biophys, Acta* 852:98–103 (1986). Preferably, at least about 10% of the tyrosine residues are hydroxylated. The mushroom tyrosinase can be removed from the protein using known procedures such as binding to a LH-Sephadex 60 column followed by elution with 0.2 M acetic acid or by membrane filtration.

While the above description, and the Examples that follow, are based upon analogs of the bioadhesive precursor protein of *M. edulis*, the invention is intended to include analogs of any and all bioadhesive precursor proteins which have a repeating structure. Utilizing techniques known to the prior art one can isolate and sequence bioadhesive precursor proteins and/or isolate and sequence the cDNA sequences encoding those proteins. Utilizing the techniques of the present invention, the skilled routineer can now deduce an appropriate DNA sequence, synthesize oligonucleotides encoding that sequence, assemble a synthetic gene coding for repeating polypeptide sequences, and express the repeating sequences. The present invention thus makes available microbial production of bioadhesive precursor protein analogs of any and all natural protein adhesives which have a repeating structure.

The bioadhesives produced by the methods of this invention can be used in a conventional manner and, if desired, may be admixed with conventional synthetic polymer adhesives, fillers, coacervates and/or adjuvants generally employed in adhesives. They are particularly useful where performance in wet environments is desired, such as marine adhesives or adhesives for medical or dental use, or protective coatings.

The bioadhesive protein can be lyophilized for reconstitution as an adhesive formulation at a later date. It can be employed as an adhesive, a sealant, or as an adhesive primer in the form of a solution in a suitable solvent with or without other adhesive substances. Suitable solvents for the bioadhesive include water or aqueous solutions of alcohols such as methanol, ethanol, propanol, and the like, acetone, DMSO, dimethyl formamide, and the like. In one embodiment the bioadhesive protein is present in the solution at a concentration from about 10 to about 50%.

A solution of the bioadhesive protein can be uniformly coated on a surface as a primer. Curing of the primer coating occurs in a normal air environment by cross-linking, which may be indicated by the development of a brown or tan color when used in high concentration. A conventional adhesive such as an epoxy adhesive is then applied over the primer coat and the surfaces to be bonded are brought together.

In another embodiment of the invention, an adhesive composition is provided that contains the hydroxylated bioadhesive protein in solution with another adhesive substance. Typical of the adhesives that may be employed in conjunction with the bioadhesive protein of the invention are the carbohydrate adhesives and the synthetic resin adhesives such as the polyacrylates, polyepoxides, resols, etc. The known carbohydrate adhesives that can be employed include chitosan, starch, pectin, glucan, dextran, etc.

A preferred carbohydrate adhesive is chitosan purified from crab or shrimp shell chitin by the procedure of Skujins, J. J. et al., *Arch. Biochem. Biophys.* 111:359 (1965). The free amino groups of chitosan are reactive with the DOPA-derived quinones of oxidized bioadhesive protein, providing covalent cross-links between the two polymers. Chitosan at appropriate concentrations provides bioadhesive protein mixtures with a high viscosity and excellent adhesive strength. The high viscosity is a particularly useful property in underwater applications where diffusion can cause a loss of material before the adhesive has an opportunity to cure.

A preferred adhesive mixture comprises from 2% to 30% of the hydroxylated bioadhesive polymer and from 1% to 7% chitosan, the balance being solvent. The pH of the composition is from about 5.5 to 7.0. The composition can be cured at pH 6.0 by the addition of catechol oxidase or tyrosinase which catalyzes the formation of DOPA-derived quinones and cross-linking.

In another embodiment of the invention, there is provided an adhesive composition in which the bioadhesive protein is admixed with other proteins that improve its physical properties such as cohesivity. The mussel adhesive protein is found closely associated with collagen in nature, thus a preferred protein for adhesive composition is collagen. A preferred composition comprises a solution having 10% to 70% solids, the solids in the solution comprising from 1% to 50% bioadhesive protein and from 50% to 99% collagen.

The bioadhesive protein of the invention is particularly useful as a biomedical adhesive or sealant, for example, in wound healing. Being a biological material, the bioadhesive protein presents a greatly reduced risk of toxic degradation products as compared with a chemical synthetic adhesive. The bioadhesive protein can be applied as a biomedical sealant in much the same manner as fibrin (see, e.g., Redl, A., and Schlag, C., *Facial Plasic Surgery* 24:315-321 (1985)).

The following examples are intended to further illustrate the practice of the invention described herein and are not intended to limit the scope of the invention.

In the examples, the method employed for the synthesis of oligodeoxyribonucleotides is the methyl-phosphite solid-phase method (Matteucci, M. D. and Caruthers, M. H., *Tetrahedron Letters*, 21:719-722 [1980]) using an automated solid-phase DNA synthesizer manufactured by Applied Biosystems, Inc. The starting materials, such as the four appropriately protected 5'-dimethoxytrityl-2'-deoxyribonucleoside- 3'-phosphoramidites as well as the solid support such as silica and controlled pore glass (CPG) (Adams, S. P., Kavka, K. S., Wykes, E. J., Holder, S. B. and Gallappi, G. R., *J. Amer. Chem. Soc.*, 105:661-663 [1983]) derivatized With appropriately protected 5,-dimethoxytrityl-2,-deoxyribonucleosides, are commercially available.

The DNA synthesis proceeds from the 3,-end to the 5'-end. For the synthesis of, for example, the single strand

5'GCG AAA CCA AGT TAC CCA CCG ACC
   TAC AAA 3' the derivatized solid support containing approximately 1 umol or protected 5'-dimethoxytrityl-2'-deoxyadenosine is loaded in a synthesis column and placed into the automated DNA synthesizer. The coupling cycle consists of detritylation of the solid support with 2% trichloroacetic acid in dichloromethane; washing with anhydrous acetonitrile; simultaneous addition of an appropriately protected 5'-dimethoxytrityl-2'-deoxyribonucleoside-3'-phosphoramidate (10 umol) in acetonitrile and tetrazole (30 umol) in acetonitrile, incubation for one minute, capping of unreacted 5'-hydroxyl groups with acetic anhydride and dimethyl-aminopyridine in tetrahydrofuran; oxidation with iodine in a mixture of tetrahydrofuran, lutidine and water [2:1:2]; and final washing with anhydrous acetonitrile. The coupling cycle is repeated until the desired length of DNA is obtained. The DNA is then partially deprotected by the treatment with thiophenoxide in dioxane/triethylamine and it is released from the solid support by several (2-4) brief treatments (5-10 minutes) with concentrated ammonium hydroxide. Completely deprotected DNA is obtained by heating the concentrated ammonium hydroxide solution at 60-65 degrees C. for 8-14 hours.

The DNA is then purified by ion-exchange and linear preparative polyacrylamide gel electrophoresis. The purified DNA is enzymatically phosphorylated at the 5'- end and characterized prior to subsequent ligation.

EXAMPLE 1

Synthesis, Cloning and Expression in *E. coli* of Sequences Encoding Bioadhesive Precursor Protein Analogs Containing Direct Repeats of a Single Decapeptide The synthetic dsDNA coding for each of the repeating decapeptide unit of sequence Ala-Lys-Pro-Ser-Tyr-Pro-Pro-Thr-Tyr-Lys can be selected from sequences in which the coding strand has the formula GCN AAR CCN (AGY or TCN) TAY CCN CCN
   ACN TAY AAR wherein G, A, T and C represent deoxyribonucleotides containing the bases guanine, adenine, thymine and cytosine, respectively; R represents a deoxyribonucleotide containing guanine or adenine; Y represents a deoxyribonucleotide containing cytosine or thymine; and N represents G, A, T or C.

For expression in *E. coli* of a protein containing repeats of the decapeptide described above, the following five double-stranded oligodeoxyribonucleotide sequences are used in preparing the dsDNA insert encoding the bioadhesive precursor protein analog.

```
5' *GCGAAACCAAGTTACCCACCGACCTACAAA
       GGTTCAATGGGTGGCTGGATGTTTCGCTTT* 5'

5' *GCGAAACCCAGCTATCCTCCGACATATAAA
       GGGTCGATAGGAGGCTGTATATTTCGCTTT* 5'

5' *GCGAAACCTTCTTATCCGCCTACCTATAAG
       GGAAGAATAGGCGGATGGATATTCCGCTTT* 5'

5' *GCGAAACCGAGTTACCCACCAACGTACAAG
       GGCTCAATGGGTGGTTGCATGTTCCGCTTT* 5'

5' *GCGAAACCGTCGTACCCGCCCACCTACAAA
       GGCAGCATGGGCGGGTGGATGTTTCGCTTT* 5'
```

These oligodeoxyribonucleotides were selected with a view toward minimizing repeated DNA sequences which might lead to deletion or recombination by the host. The five oligodeoxyribonucleotides are ligated to each other randomly in order to produce a sequence coding for various repeats of the decapeptide.

The automated DNA synthesizer is employed to synthesize the ten single-stranded oligodeoxyribonucleotides having the sequences shown above. There are also synthesized two single-stranded oligodeoxyribonucleotides which can be annealed to form the following blunt-ended linker fragment for the 5' end of the dsDNA insert.

```
                    BamHI
        5' CTA GAG GGA TCC ATG
            GAT CTC CCT AGG TAC CGC TTT* 5'
                            NcoI
```

Finally, there are synthesized two single-stranded oligodeoxyribonucleotides which can be annealed to form the following blunt-ended linker fragment for the 3' end of the dsDNA insert.

```
                    Stop
        5' *GCG AAA TGA ATT C
                ACT TAA G 5'
                    EcoRI
```

The 5' ends of the single-stranded oligodeoxyribonucleotides labeled with asterisks are phosphorylated by treatment with adenosine triphosphate in the presence of polynucleotide kinase.

To produce a protein containing 20 repeats of the decapeptide, the ten oligodeoxyribonucleotides (1.6 ug each) representing the decapeptide and the four linker oligodeoxyribonucleotides (0.4 ug each) are annealed and ligated in the presence of T4 DNA ligase. The ligation reaction produces a family of blunt-ended dsDNAs of varying length having an average of about 20 of the decapeptide-encoding fragments, ligated in random order, preceded and followed by the 5' and 3' linker fragments, respectively. The synthetic dsDNA thus produced encodes a series of repeated decapeptides directly preceded by the sequence Leu-Glu-Gly-Ser-Met, encoded by the 5' linker and followed by the dipeptide Ala-Lys, encoded by the GCGAAA sequence preceding the stop codon (TGA) in the 3' linker. The synthetic dsDNA from the ligation reaction is run on a 6% polyacrylamide gel according to the procedure of Maniatis, et al. (*Biochemistry*, 14:3787-3794 [1975]. The band corresponding in size to 20 decapeptide-encoding sequences is cut from the gel and the dsDNA is electroeluted from the gel. If it is desired to produce a protein having fewer or greater than 20 decapeptide repeats, then the ratio of oligodeoxyribonucleotide fragments representing the decapeptide to linker fragments in the ligation mixture is adjusted proportionately and the dsDNA fragment of desired size is isolated from the gel.

Figure 4:
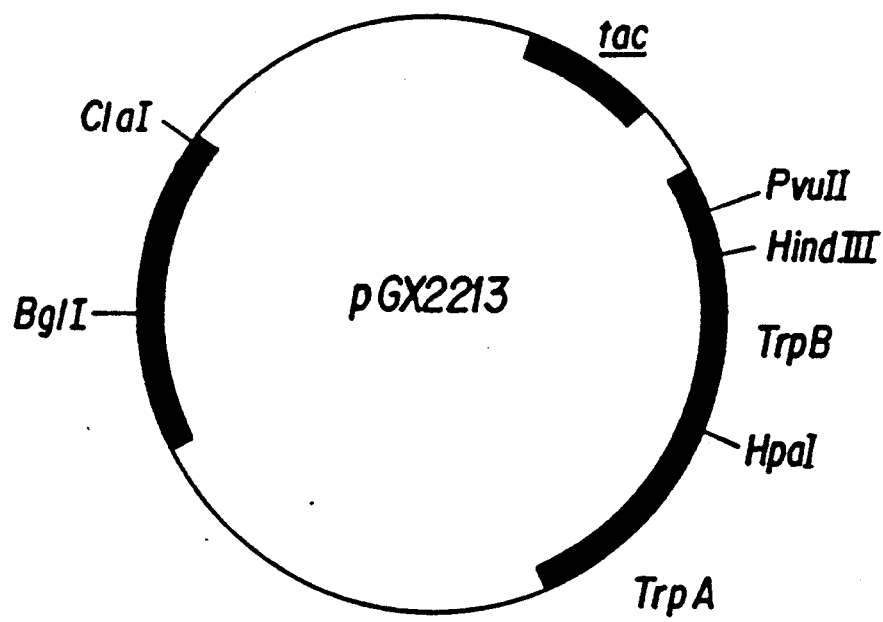
FIG. 4 is a diagram of E. coli plasmid pGX2213, containing the trpB and trpA regions of the tryptophan synthetase operon and the tac promoter.

The synthetic dsDNA sequence is then inserted into the single HpaI site of plasmid pGX2213. Referring to FIG. 4, this plasmid contains the trpB and trpA regions of the tryptophan synthetase operon under the control of a tac (hybrid trp/lac) promoter. The plasmid has been deposited, in an *E. coli* host (strain GX1668), at the American Type Culture Collection, Rockville, Md., with accession number ATCC 39388. The plasmid (1 ug) is cleaved by treatment with HpaI unit). Cleavage occurs within the trpB region, leaving 1122 base pairs at the 5' end of the trpB gene linked to the tac promoter. The linearized plasmid has blunt ends. The dsDNA insert containing the decapeptide-encoding sequences (0.2 ug) is blunt-end ligated to the linearized pGX2213 using T4 DNA ligase.

The recircularized plasmids are used to transform *E. coli* strain JM109. This host strain is commerically available, e.g., from P-L Biochemicals, Inc., Bethesda Research Laboratories, Inc. and New England BioLabs, Inc. It contains the lacI<sup>q</sup> gene which overproduces the lac repressor protein which regulates expression from the tac promoter. Expression from the tac promoter can be induced by the addition of isopropyl--D-thiogalactoside (IPTG). The host is also recA-, which reduces the likelihood of recombination of repeated decapeptide-encoding sequences in the dsDNA insert. The transformed *E. coli* JM109 cells are inoculated onto LB-agar plates containing ampicillin and grown for 24 hours. Plasmid DNA prepared from the resultant colonies is screened by restriction analysis to isolate clones containing a single dsDNA insert in the proper orientation. The isolated clones contain a fused gene which codes for a protein containing the first 374 amino acids of the trpB gene product fused to the five amino acids coded for by the linker at the 5' end of the synthetic dsDNA insert (Leu-Glu-Gly-Ser-Met), followed by twenty repeats of the decapeptide sequence of the insert and terminating with Ala-Lys, which is coded for by the portion of the linker at the 3' end of the synthetic insert preceding the stop codon.

Transformants containing the single dsDNA insert in the proper orientation are inoculated into 2-liter culture flasks containing Luria broth and ampicillin and are grown to mid-log phase (OD600 0.5). IPTG (0.25 mM, final concentration) is added to induce expression. After 8-16 hours, the fusion protein is expressed at high levels in the host cells. The cells are harvested by centrifugation, lysed by sonication, and the fusion protein is recovered by conventional protein recovery techniques. The fusion protein is treated with cyanogen bromide, which cleaves the protein on the carboxyl side of the methionine residue immediately preceding the first decapeptide sequence, thereby separating the bioadhesive precursor protein from the N-terminal fragment of the trpB gene product and the linker-derived peptide fragment. The bioadhesive precursor protein is then isolated by conventional procedures.

EXAMPLE 2

Synthesis, Cloning and Expression in *S. cerevisiae* of Sequences Encoding Bioadhesive Precursor Protein Analogs Containing Direct Repeats of a Single Decapeptide For expression in *S. cerevisiae*, the following double-stranded oligodeoxyribonucleotide sequence is used in preparing the dsDNA insert encoding the bioadhesive precursor protein analog.

```
GCTAAGCCATCTTACCCACCAACCTACAAG
    GGTAGAATGGGTGGTTGGATGTTCCGATTC
```

The automated DNA synthesizer is used to synthesize the following oligodeoxyribonucleotides:

```
A  5'  GCT AAG CCA TCT TAC CCA CCA ACC TAC AAG
B  5'  CTT AGC CTT GTA GGT TGG TGG GTA AGA TGG
C  5'  GAA TTC GTC GAC ATG
D  5'  CTT AGC CAT GTC GAC GAA TTC
E  5'  GCT AAG TAA GCT TGG ATC C
F  5'  GGA TCC AAG CTT A
```

Oligodeoxyribonucleotides A, B, D and E are phosphorylated at the 5' ends by treatment with adenosine triphosphate in the presence of polynucleotide kinase. To produce a protein containing 20 repeats of the decapeptide, the oligodeoxyribonucleotides are annealed and ligated in the presence of T4 DNA ligase at a ratio of 4A:4B:1C:1D:1E:1F to produce a dsDNA insert comprising a 5' linker (C and D), a 3' linker (E and F) and a repeated decapeptide coding sequence (A and B) which contains the preferred codons for expression in *S. cerevisiae*. The 5' linker contains EcoRI and SalI cleavage sites. The 3' linker contains HindTTT and BamHI cleavage sites. The ligation product is run on a 6% polyacrylamide gel according to the procedure of Maniatis et al., supra. The band corresponding to a dsDNA having approximately 20 repeats of the decapeptide coding sequence is cut from the gel and dsDNA is electroeluted from the gel.

Figure 5:
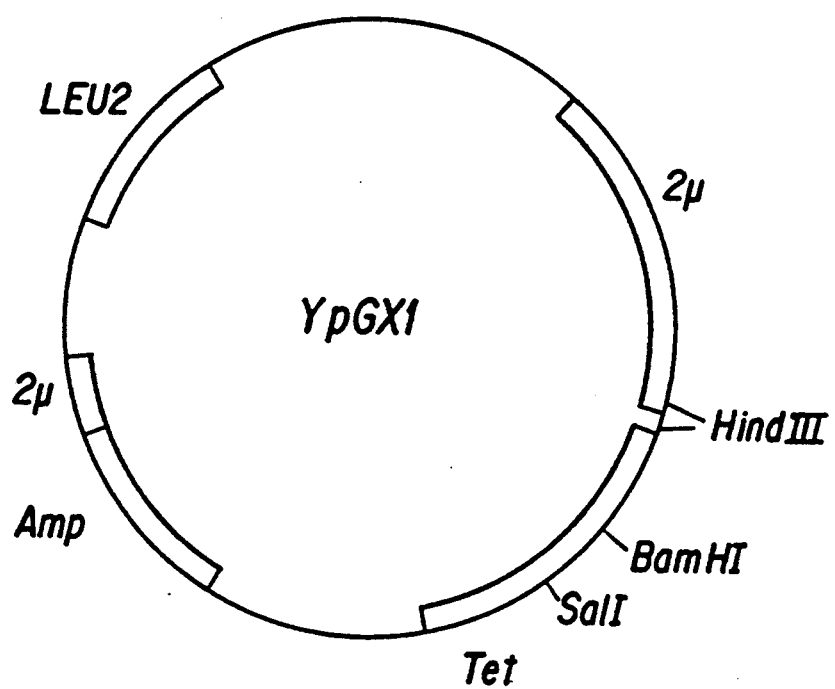
FIG. 5 is a diagram of S. cerevisiae-E. coli shuttle vector YpGX1.

The isolated dsDNA fragment is digested with SalI and HindIII to generate staggered ends. The dsDNA fragment thus produced is inserted into YpGXI, which is represented in FIG. 5. YpGXI has unique SalI and HindIII restriction sites within the tetracycline resistance gene. The plasmid (2 ug) is digested with SalI and HindIII and the resulting linearized plasmid is ligated with the dsDNA insert in the presence of T4 DNA ligase. The recircularized plasmid is used to transform *E. coli* strain JM109 and the transformants are grown separately on LB-agar plates containing ampicillin and then transferred onto LB+ ampicillin and LB+ tetracycline plates. Plasmids from the Ap$^R$Tc$^S$ colonies are analyzed by restriction endonuclease digestion to identify those plasmids containing the dsDNA insert in the proper orientation.

Figure 6:
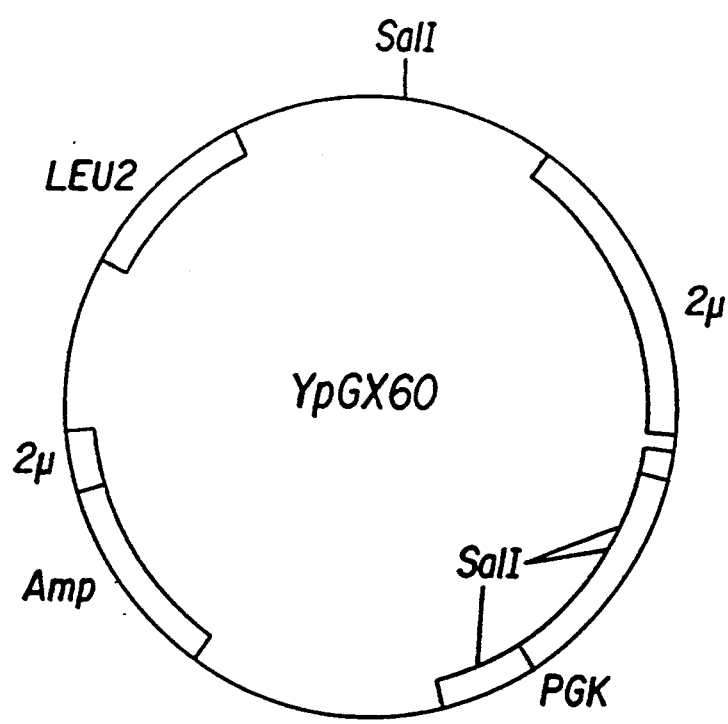
FIG. 6 is a diagram of S. cerevisiae plasmid YpGX60 containing a portion of the phosphoglycerate kinase gene.

An *S. cerevisiae* phosphoglycerate kinase (PGK) promoter and partial structural gene fragment is isolated from plasmid YpGX60, which is represented in FIG. 6. YpGX60 is digested with SalI and the 2000-base pair fragment corresponding to the PGK promoter and the first 229 codons of the structural gene is isolated by gel electrophoresis. The plasmid YpGXl into which the synthetic dsDNA fragment encoding 20 repeats of the decapeptide has been inserted is digested with SalI. The PGK fragment isolated from plasmid YpGX60 is ligated to the linearized YpGXI containing the 20 decapeptide coding insert in the presence of T4 DNA ligase. The resulting plasmid is used to transform an *S. cerevisiae* strain such as D8 or AH22 (ATCC #38626). The transformants are grown on YNBD solid medium supplemented with appropriate nutrients and screened immunologically to identify colonies that produce the PGK-adhesive fusion protein. The isolated transformants are inoculated into 2-liter flasks containing YNBD+ tryptophan and grown overnight at 30° C. The cells are harvested by centrifugation and lysed in a French press. The fusion protein is recovered by conventional protein recovery techniques and treated with cyanogen bromide, which cleaves the protein on the carboxyl side of the methionine residue immediately preceding the first decapeptide sequence, to separate the bioadhesive precursor protein from the N-terminal fragment of PGK and the linker-derived peptide. The bioadhesive precursor protein is then isolated by conventional procedures.

EXAMPLE 3

Production of Antibody to Bioadhesive Precursor Protein Analogs

Synthetic decapeptide (1.5 mg) of sequence Ala-Lys-Pro-Ser-Tyr-Pro-Pro-Thr-Tyr-Lys, prepared by the Merrifield solid-state method, was combined with 2.0 mg of bovine serum albumin (BSA) in 1.8 ml phosphate-buffered saline. One percent glutaraldehyde (0.2 ml) was added and the solution was incubated 30 minutes at 22° C. Sodium borohydride was added to a final concentration of 0.5 mg/ml and incubation was continued at 22° C. for one hour. The solution was then dialyzed against phosphate-buffered saline. Amino acid analysis of the resulting protein indicated 35 moles of peptide were coupled per mole of BSA.

Rabbits were given intramuscular injections with 100 ug of peptide (BSA coupled) in incomplete Freund's adjuvant. Booster subcutaneous injections using incomplete Freund's adjuvant were given subsequently in two-week intervals. Antiserum with high-titer antibody reactive toward the decapeptide as well as *M. edulis* bioadhesive precursor protein isolated from mussels or analog proteins produced in microorganisms was obtained by this method.

EXAMPLE 4

Figure 7:
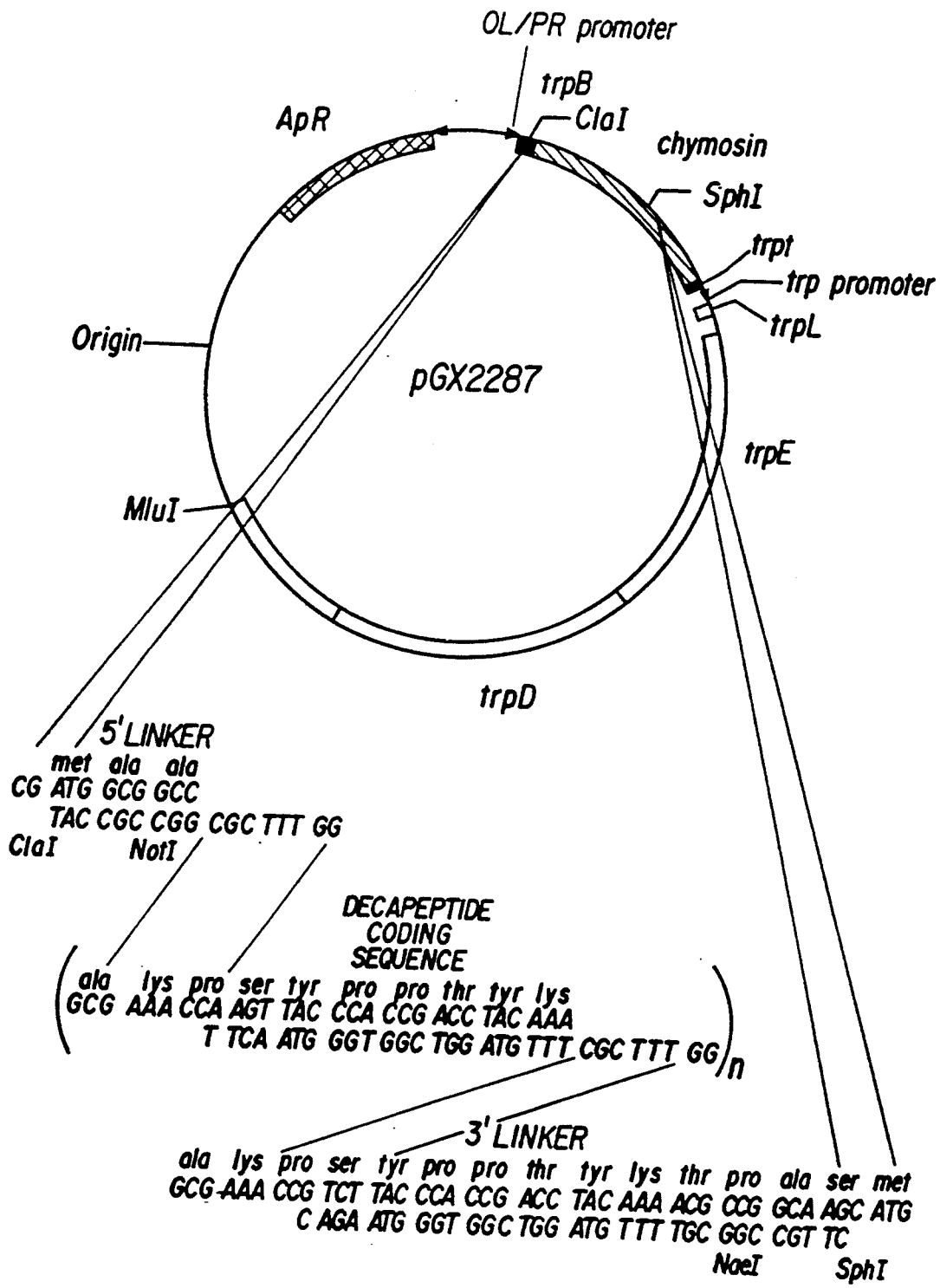
FIG. 7 depicts a method of inserting synthetic DNA sequences encoding bioadhesive precursor protein analogs into E. coli plasmid pGX2287 to generate coding sequences for a tribrid fusion protein.

Synthesis, Cloning and Expression in *E. coli* of Sequences Encoding Bioadhesive Precursor Protein Analogs Containing Repeats of a Single Decapeptide A. *Assembly of pGX2346*. Plasmid pGX2287 (NRRL-B15788), part of a vector/host system for expression of bovine chymosin, was used as the *E. coli* cloning and expression vector for bioadhesive precursor protein analog coding sequences. FIG. 7 outlines the DNA pieces that were assembled during initial cloning experiments. Synthetic DNA coding for one decapeptide flanked by 5' and 3' linkers was cloned between unique ClaI and SphI endonuclease sites of pGX2287 such that a synthetic tribrid gene was formed, containing a 5' segment of the efficiently expressed trpB gene, the bioadhesive precursor protein analog coding sequence and a 3' region encoding 159 carboxy terminal amino acids of bovine chymosin. This tribrid gene was utilized because the 5' sequence and trpB portion provides efficient transcription and translation initiation, and the chymosin sequence causes the formation of insoluble inclusion bodies in *E. coli*. Inclusion body formation can lend stability to a foreign protein and provide a convenient method of initial purification. Methionine codons were situated on either side of the bioadhesive precursor protein analog coding sequence, so that the bioadhesive precursor protein can be easily excised from the resulting fusion protein by treatment with cyanogen bromide.

The synthetic DNA shown in FIG. 7 was synthesized as seven oligonucleotides using an Applied Biosystems DNA synthesizer (phosphoramidite chemistry). These oligonucleotides were designated:

| Oligonucleotide Number | Sequence | Function |
| --- | --- | --- |
| 1875 | GGTTTCGCGGCCGCCAT | 5' linker |
| 1876 | CGATGGCGGCC | 5' linker |
| 1877 | CTTGCCGGCGTTTTGTAGGTCGGTGGGTAAGAC | 3' linker |
| 1892 | GCGAAACCGTCTTACCCACCGACCT | 3' linker |
| 1893 | ACAAAACGCCGGCAAGCATG | 3' linker |

| Oligonucleotide Number | Sequence | Function |
| --- | --- | --- |
| 1545 | GCGAAACCAAGTTACCCACCGACCTACAAA | decapeptide sequence |
| 1546 | GGTTTCGCTTTGTAGGTCGGTGGGTAACTT | decapeptide sequence |

After purification by preparative gel electrophoresis and reverse-phase chromatography, the oligonucleotides were dissolved at a concentration of 1 delta 280 unit/ml. Oligonucleotides #1876, #1988, and #1892 were phosphorylated individually in reactions with T4 polynucleotide kinase and 1 mM ATP with 20 ul of oligonucleotide solution added in a 50 ul kinase reaction. Oligonucleotides #1545 and #1546 were similarly treated, except they were pooled first at a 1:1 ratio. After the enzyme reaction, the solutions were boiled for two minutes to inactivate the enzyme. An equivalent amount of oligonucleotide #1875 was added to the #1876 kinase reaction, boiled for 30 seconds, then allowed to slow cool for formation of 5' linker Likewise, the #1892 and #1877 kinase reactions were mixed together with an equivalent amount of non-kinased #1893, boiled, slow cooled and then ligated in a 180 ul volume at 16° C. for 11 hours with T4 polynucleotide ligase to assemble the 3' linker. Plasmid pGX2287 DNA (5 ug) was digested with 18 units of ClaI endonuclease then extracted with phenol-chloroform, ethanol precipitated and dissolved in 0.01 M Tris-HCl, 0.001 M EDTA (pH 8.0) at 0.25 ug DNA/ul. Ten microliters of the ClaI-cut pGX2287 DNA was ligated with 25 ul of the 5' linker in a total volume of 40 ul at 16° C. for 11 hours. After ligation, the DNA was phenol-chloroform extracted, ethanol precipitated, then dissolved in 1 ml water. The DNA solution was concentrated using a Centricon 30 (Amicon) ultrafiltration unit, then washed two times with 2 ml water and centrifuged at 5,000 RPM for ten minutes. The washed and concentrated DNA, largely free of non-ligated linkers, was ethanol precipitated and dissolved in 10 microliters of water.

Three micrograms of the above ClaI-cut pGX2287 DNA with attached 5' linker was ligated in a 20 ul volume with 10 ul of the solution of kinased decapeptide coding DNA segments (oligonucleotides #1545 and #1546) at 22° C. After 40 minutes, 20 ul of the 3' linker ligation mixture (#1877, #1892, and #1893) was added and the ligation was continued for 12 hours at 22° C.

The ligation mixture was diluted to 150 ul in SphI endonuclease buffer and digested with SphI. Ten micrograms of tRNA was added, the solution was phenol-chloroform extracted, then ethanol precipitated. The DNA was finally dissolved and diluted to 200 ul in T4 ligase buffer and ligated at 15° C. overnight. The ligation was used to transform E. coli GX3015 (F− trpED102 tna2 recA nadA [ch1D-pg1] [lambda cI857 BamH1) using standard procedures. Any other E. coli host is suitable that has recA, trpED mutations, and has a defective lambda lysogen with the lambda cI857 repressor. Cells were grown at 30° C. on LB +100 ug/ml ampicillin or minimal medium containing 0.4% glucose, 0.4% acid hydrolyzed casein (casamino acids, Difco), and 100 ug/ml ampicillin. One characterized transformant, upon heating to 37° C., produced a protein that reacted with both anti-chymosin antibody and anti-decapeptide antibody (produced in accordance with Example 3) in Western blot experiments (Burnette, W. N., 1981, *Anal. Biochem.*, 112:195-203). The plasmid in this transformant was named pGX2346 and DNA sequence analysis demonstrated that the synthetic gene contained a 5' and 3' linker with two internal decapeptide coding segments for a total of three decapeptide coding segments (one of these decapeptides is encoded by the 3' linker, see FIG. 7).

B. Increasing the size of the bioadhesive precursor protein analog coding sequence to construct pGX2348. The 5' and 3' linkers flanking the three decapeptide coding sequence in pGX2346 were designed with unique restriction sites such that the size of the bioadhesive precursor protein analog coding sequence could be increased through a simple ligation procedure without requiring further oligonucleotide ligations. The 5' linker contains a NotI site and the 3' linker contains a NaeI site. The 5'-end of the three decapeptide coding sequence generated by NotI digestion of pGX2346 followed by treatment with DNA polymerase I was ligated to the blunt 3'-end of the three decapeptide coding sequence generated by NaeI digestion of second aliquot of pGX2346 (see FIG. 2). This creates an in-frame fusion through a linker region that codes for thr-pro-ala. The 5', 3' and internal linkers all code for amino acids (ala, thr, pro, ser) that are used in the prototype decapeptide and thus do not disrupt the general characteristics of the translation products.

About 0.5 ug of pGX2346 DNA was cut with NotI in a volume of 20 ul. A second 0.5 ug aliquot of pGX2346 DNA was cut with NaeI. The DNA solutions were extracted with phenolchloroform, ethanol precipitated and dissolved in 20 ul of water. The I-digested DNA was reacted with T4 DNA polymerase in a 100-ul reaction with 0.25 mM dATP, dGTP, dCTP, dTTP at 37° C. for 30 minutes to fill in the NotI-generated single-stranded end. The DNA was extracted, precipitated and dissolved in water. About half of the NotI/PolI treated DNA and half of the NaeI-treated DNA were ligated together in a 20-ul volume at 22° C. for 4.5 hours with T4 polynucleotide ligase and 0.5 mM ATP. The ligation was diluted to 100 ul with PvuI buffer and digested with 28 units of PvuI for one hour at 37° C. Carrier tRNA (20 ug) was added, and the reaction was extracted and precipitated. Finally, the DNA was ligated at 15° C. for 8 hours in a volume of 150 ul to promote circular DNA formation at low DNA concentration. GX3015 cells were transformed with the ligation mixture.

One transformant that was characterized had a plasmid shown by DNA sequencing to encode a bioadhesive precursor protein analog of five decapeptide repeats instead of the expected six repeats. Also the thr-pro-ala coding sequence expected to result from joining 5' and 3' linkers was not present. The likely explanation for this observation is that one decapeptide coding repeat and the linker were lost in a homologous recombination event. The new plasmid was designated pGX2348. When cells containing pGX2348 are grown at 30° C., then shifted to 37° C., they produce a 27,000 molecular weight protein that reacts with anti-decapeptide antibody, as expected.

C. Further expansion of the bioadhesive precursor protein analog coding sequence. Plasmid pGX2348 with a five-decapeptide coding sequence was taken through the same ligation procedure described for pGX2346 above, resulting in a transformant containing plasmid pGX2354, with exactly the predicted structure (see FIG. 8). There are two segments that each code for five tandem decapeptide repeats separated by a thr-pro-ala tripeptide coding sequence. The joining of the 5' and 3' linkers at the NotI and NaeI sites regenerates the NaeI site. Therefore, further use of the ligation procedure described above resulted in size increases in increments of five-decapeptide coding repeats. Thus, pGX2354 10-decapeptide repeats) was used for the construction of pGX2358 (15-decapeptide repeats) and pGX2358 was used for the construction of pGX2365 (20-decapeptide repeats). Although the DNA sequence of the inserts in pGX2358 and pGX2365 were not determined, they have internal NaeI sites and also produce immunoreactive proteins of the expected molecular weights before and after cyanogen bromide cleavage, as shown below. These data are consistent with synthetic genes of the expected structure, i.e., tandem decapeptide coding repeats separated by a tripeptide coding segment.

| Plasmid | Number Decapeptide Repeats | Precursor Protein Analog M.W. | CNBr-Cleaved Precursor Analog M.W. |
|---|---|---|---|
| pGX2346 | 3 | 24,729 | 4,004 |
| pGX2348 | 5 | 26,996 | 6,270 |
| pGX2354 | 10 | 32,931 | 12,206 |
| pGX2358 | 15 | 38,854 | 18,128 |
| pGX2365 | 20 | 44,803 | 24,077 |

FIG. 9 shows the amino acid sequence of the 24,077 molecular weight bioadhesive precursor protein analog produced by cells containing plasmid pGX2365 after cyanogen bromide cleavage.

D. Analysis of the Decreased Bioadhesive Precursor Protein Analog Accumulation with Increasing Decapeptide Repeat Length. Based on the intensity of immunological reaction in Western blots (FIG. 10), and Coomassie-stained total cellular protein (data not shown), the *E. coli* cells with plasmids pGX2346 and pGX2348 produced the bioadhesive precursor protein as several percent of the total insoluble protein, but as the number of decapeptide repeats was increased to 10, 15 and 20, significantly less protein was produced. That is, the gene expression level was inversely dependent on the number of encoded decapeptide repeat units. The plasmid series pGX2346 through pGX2365 with three to twenty repeats were constructed to be identical, except for the length of the synthetic bioadhesive precursor protein gene. Therefore, it seems likely that the decreased expression level is associated directly with the increased size of the expressed gene.

E. Fermentation of *E. coli* strains for production of the bioadhesive precursor protein analog. Plasmid pGX2287 contains the bla gene which encodes beta-lactamase, providing ampicillin resistance, as well as the trpED genes that in trytophan-deficient medium complement the trpED102 deletion in the host GX3015 chromosome. Transformed cultures of *E. coli* GX3015 were grown with 100 ug/ml ampicillin and/or in medium lacking tryptophan.

A single colony of GX3015 containing one of the plasmids described in Section C above is picked after growth on minimal salts medium (Miller, J. H., "Experiments in Molecular Genetics," Cold Spring Harbor Laboratory, 1972, p.432) supplemented with 0.4% casamino acids and 0.4% glucose and inoculated into 5 ml of LB medium supplemented with 100 ug/ml ampicillin. After reaching an optical density (A600) of greater than 1.0, 0.4 ml of the culture is inoculated into each of two 250-ml baffled flasks containing 50 ml of LB broth supplemented with 100 ug/ml ampicillin. The two flasks are incubated at 30° C. and shaken at 250 RPM for 6.5 to 9 hours.

Fermentation is carried out using eight liters of the following initial medium:

$(NH_4)_2SO_4$—30 g
$KH_2PO_4$—15 g
$K_2HPO_4$—5 g
Biotin (0.5 mg/ml in 95% ethanol)—12 ml
Add tap water to eight liters, autoclave.

The following additions are made after autoclaving to provide the initial medium:
$CaCl_2 2H_2O$—10 ml of 10% (w/v) sterile solution
glucose—360 ml of 50% (w/v) sterile solution
niacin—18 ml of 0.5% (w/v) sterile solution
Trace solution 1–90 ml
Trace solution 2–18 ml
Trace solution 3–1.8 ml The following fermentation conditions are maintained:
pH-7.0 (controlled by 5N $NH_4OH$, and 1N $H_3PO_4$)
Sparge rate—1 vvm
Temperature—32° C.
Agitation rate—800 r.p.m.

In order to increase cell density prior to induction of expression, a system of broth supplementation with nutrients is undertaken. The feed solution is prepared as follows:

A solution of 1,000 g glucose in deionized water (final volume of 1700 ml) is autoclaved. After autoclaving, trace mineral solutions are added:
Trace Solution 1–500 ml
Trace Solution 2–100 ml
Trace Solution 3–10 ml
$CaCl_2.2H_2O$ 50 ml

| Trace Solution 1 | |
|---|---|
| $H_2O$ | 900 ml |
| conc HCl | 13.1 ml |
| $FeCl_2.6H_2O$ | 5.4 g |
| $ZnSO_4.7H_2O$ | 1.44 g |
| $MnCl_2.4H_2O$ | 1.0 g |
| $CuSO_4.5H_2O$ | 0.25 g |
| $CoCl_2.6H_2O$ | 0.24 g |
| $H_3BO_3$ | 0.062 g |

Brought to 1000 ml and sterile filtered.

| Trace Solution 2 | |
|---|---|
| $H_2O$ | 900 ml |
| HCl | 44.8 ml |
| $MgSO_4.7H_2O$ | 61.6 g |

Brought to 1000 ml and sterile filtered.

| Trace Solution 3 | |
|---|---|
| $H_2O$ | 1000 ml |

| -continued |
|---|
| Trace Solution 3 |
| Na$_2$MoO$_4$.2H$_2$O    24.1 g |

Sterile filtered.

The feed solution is initially added to the broth in a volume of 180 ml and thereafter as needed to maintain the glucose level at 10 g/liter. Feed supplementation is continued until the A600 reaches 20, at which time the cells are induced to express the tribrid bioadhesive precursor protein gene from the hybrid lambda O$_L$/P$_R$ promoter. Induction is effected by raising the temperature to 42° C. for one hour to deactivate the temperature-sensitive lambda cI857 repressor protein produced by the defective lambda lysogen in the GX3015 chromosome. The fermentation is continued at 37° C. for another 6–8 hours.

EXAMPLE 5

Experiments to Improve the Expression of the Bioadhesive Precursor Protein Analog Containing Twenty Repeats of the Decapeptide (Ala-Lys-Pro-Ser-Tyr-Pro-Pro-Thr-Tyr-Lys)

Plasmid pGX2365 was further manipulated in attempts to increase expression of the 20-repeat protein in E. coli. In particular to examine the effect of chymosin sequences on expression level and intracellular solubility, two new variants of pGX2365 were prepared as described below.

Plasmid pGX2365 has a unique SphI site at the end of the decapeptide multimer coding sequence, a unique BanII site within the chymosin coding sequence and a unique BclI site at the end of the chymosin coding sequence. Oligonucleotides were synthesized and annealed to yield the linker shown below that could be used for stepwise deletion of chymosin sequences from the gene.

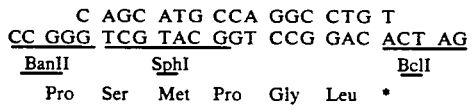

```
    C AGC ATG CCA GGC CTG T
CC GGG TCG TAC GGT CCG GAC ACT AG
   BanII    SphI            BclI
   Pro Ser Met Pro Gly Leu  *
```

The linker was first inserted between the BanII and BclI sites of pGX2365 to create pGX2374. The protein produced from pGX2374 has only 61 carboxy-terminal amino acids derived from chymosin plus four linker amino acids. The deletion removed the 98 carboxy-terminal chymosin amino acids, including two of the four cysteines originally present in the chymosin segment. Digestion of pGX2374 with SphI followed by removal of the small SphI fragment and recircularization resulted in deletion of the remaining chymosin sequences, leaving only the carboxy-terminal amino acids met-pro-gly-leu encoded by the linker sequence after the decapeptide repeats. This plasmid was designated pGX2375.

Figure 10:
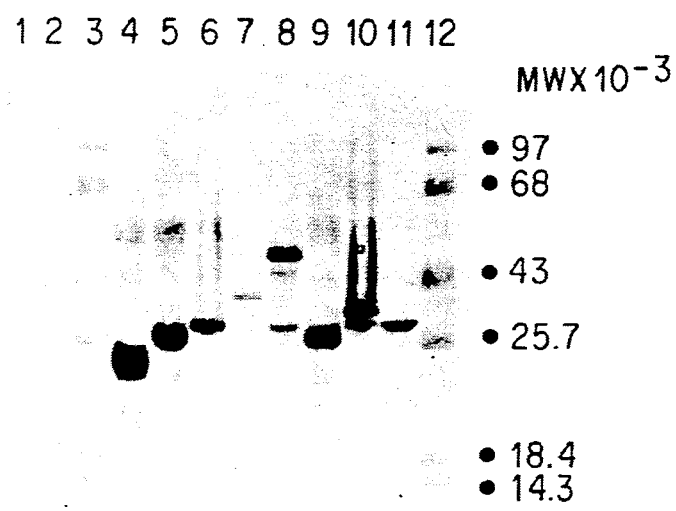
FIG. 10 represents a Western blot analysis (Total lysate (soluble and insoluble) for several bioadhesive precursor protein analogs produced in E. coli. Lane 1; pGX2365 uninduced; lane 2:pGX2375 uninduced; lane 3: molecular weight standards; lane 4; pGX2346 induced; lane 5; pGX2348 induced; lane 6: pGX2354 induced; lane 7:pGX2358 induced; lane 8: pGX2365 induced; line 9: pGX2367 induced; lane 10: pGX2374 induced; lane 11; pGX2375 induced; lane 12: molecular weight standards.

The expression level and solubility of decapeptide multimer protein produced with pGX2374 and pGX2375 was compared with all the earlier plasmids in the Western blots shown in FIG. 10.

EXAMPLE 6

Expression in *Saccharomyces cerevisiae* of Sequences Encoding Bioadhesive Precursor Protein Analogs Containing Repeats of a Single Decapeptide Bioadhesive precursor protein analog sequences constructed as in Example 4 were incorporated into the yeast expression vector YpGX265GAL4 (ATCC #67233) shown in FIG. 3. This yeast-*E. coli* shuttle vector replicates at very high copy number (100–200 copies per cell) in Saccharomyces because it carries the yeast 2 micron replication origin and LEU2-d allele from pJDB207 (Beggs, J. D., In Alfred Benzon Symposium 16, Molecular Genetics in Yeast, Von Wettstein, D. et eds., Munksgaard, Copenhagen, pp. 383–389 (1981)). Transcription initiation and regulation are determined by a promoter that is a hybrid composed of the MF-alpha1 transcription initiation site (TIS) coupled with the upstream activation site (UAS) from the GAL1-10 regulatory region. In order for transcription initiation to occur efficiently, the GAL1-10 UAS must bind GAL4 protein, a positive regulator of yeast galactose genes. In order to provide sufficient GAL4 protein to bind the multiple GAL1-10 UAS sites, the GAL4 gene is also carried on the expression plasmid. In addition, plasmid YpGX265GAL4 contains a signal encoding sequence derived from the PH05 gene. To terminate transcription, a synthetic terminator based on that found in a yeast glyceraldehyde 3-phosphate dehydrogenase (GAPDH) gene was utilized.

Figure 11:
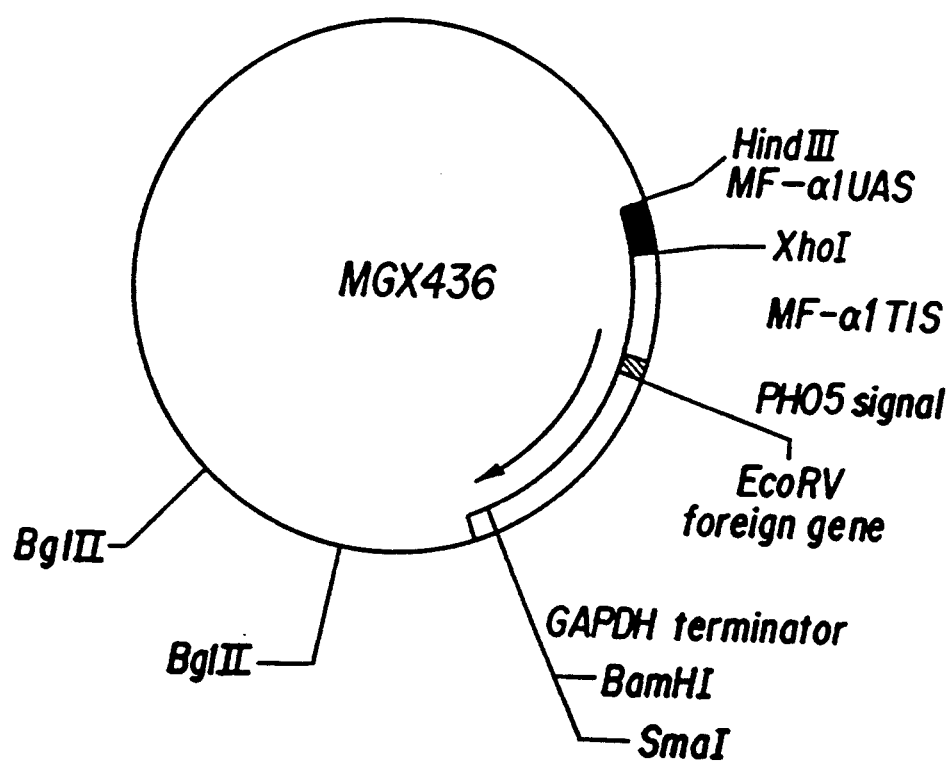
FIG. 11 is a diagram of an M13-based Vector, MGX436, containing the S. cerevisiae MF-alpha promoter (UAS: upstream activation site; TIS, transcription initiation site).

The yeast expression module from vector YpGX26-2GAL4 (fully described in U.S. Pat. No. 5,013,652 was excised with restriction enzymes HindIII and BamHI and cloned into M13mp9 to generate MGX436 (see FIG. 11).

The bioadhesive precursor protein analog-chymosin hybrid gene with its *E. coli* regulatory sequences was excised from pGX2365 (see Example 4) using SmaI and BclI restriction endonucleases and was joined at the EcoRV and BamHI sites in the yeast expression module in MGX436 to generate MGX441. The *E. coli* sequences except for the five trpB codons and the methionine codon directly preceding the analog sequence were deleted by oligonucleotide-directed mutagenesis using the following oligonucleotide sequence:

```
5'
CATCGATGGCTGGCGCAGAGCGTTGG-
CCAAAGAAGC
```

This generated vector MGX448.

The yeast expression module-bioadhesive precursor protein analog-chymosin sequence was excised from the MGX448 vector using SmaI and XhpI restriction endonucleases and transferred to the yeast-*E. coli* shuttle vector to generate YpGX277. The GAL4 gene was then added to YpGX277 as a HindIII fragment at the unique HindIII site to generate YpGX277GAL4. The bioadhesive precursor protein analog encoded by this plasmid has the sequence PH05 signal-leu-arg-gln-pro-ser-met-ala-ala [(ala-lys-pro-ser-tyr-pro-pro-thr-tyr-lys)$_5$thr-pro-ala]$_4$-ser-met-chymosin(159 amino acids).

To assemble a yeast expression vector in Which the PH05 signal and bioadhesive precursor protein sequences are separated by a methionine codon but without trpB codons, pGX2365 was digested with ClaI and BclI and the fragment containing the bioadhesive precursor protein analog sequence was gel purified. In addition, two oligonucleotides of sequence 5'ATCAAT and 5' CGATTTGAT were synthesized and annealed. MGX436 double-stranded DNA was digested with EcoRV and BamHI and the large vector fragment was gel purified.

The two purified DNA fragments and the annealed oligonucleotides were ligated and E. coli was transformed using standard protocols. Only one plaque contained DNA which digested with BamHI and EcoRV to release a DNA fragment.

Restriction endonuclease and DNA sequence analysis revealed that the linker oligonucleotides were inserted as expected, but that the bioadhesive precursor protein region had expanded by a recombination event so that a 30-repeat decapeptide sequence, rather than the expected 20-repeat was encoded by the vector. The bioadhesive precursor protein analog coding sequence and the yeast expression module were excised from this M13 vector using the SmaI and XhoI sites at the 5'- and 3'-ends respectively, and ligated with the yeast E. coli shuttle vector to generate YpGX275. The GAL4 gene was then added as a HindIII fragment at the unique HindIII site to generate YpGX275GAL4. The bioadhesive precursor protein encoded by YpGX275GAL4 is PH05 signal-asp-ile-lys-ser-met-ala-ala-[(ala-lys-pro-ser-tyr-pro-pro-thr-tyr-lys)₅thr-pro-ala]₆-ser-met-chymosin(159 amino acids).

To remove the chymosin sequence from the 3'-end of the bioadhesive precursor analog coding sequence in YpGX277GAL4, a fragment containing the yeast promoter, signal sequence and bioadhesive precursor protein analog sequence was excised from YpGX277GAL4 using the HindIII site at the start of the promoter and the SphI site separating the bioadhesive precursor analog sequence from the chymosin sequence. This fragment Was cloned into M13mp18 such that the SphI site is adjacent to a BamHI site. The fragment containing the yeast promoter-signal sequence bioadhesive precursor protein analog sequence was then excised from the double-stranded M13 vector using the HindIII site at the start of the promoter region and the BamHI site from M13. This fragment was then ligated with the yeast E. coli shuttle vector and the GLA4 gene was added as a HindIII fragment to generate an expression vector, YpGX279GAL4 which is equivalent to YpGX265GAL4 but with the bioadhesive precursor protein analog sequence positioned between the EcoRV site at the end of the PH05 signal encoding sequence and the BamHI site preceding the GAPDH terminator. In the same manner the chymosin coding region was deleted from YpGX275GAL4 to generate YPGX283GAL4.

In order to generate an expression vector without the trpB codons between the PH05 signal and the bioadhesive precursor protein analog sequence, but encoding a 20-repeat decapeptide sequence, the following construction was performed.

Figure 12:
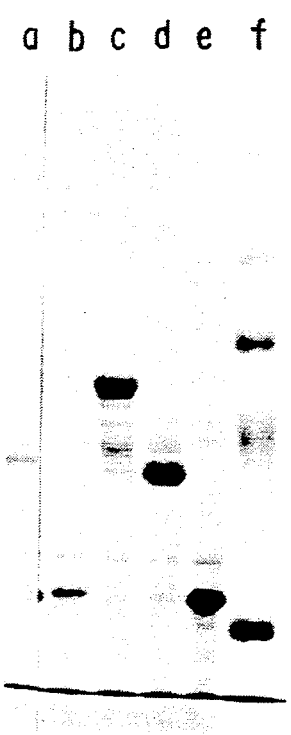
FIG. 12 represents SDS-polyacrylamide gel analysis for several bioadhesive precursor protein analogs produced in S. cerevisiae Lane a: plasmid YpGX277GAL4; lane b: plasmid YpGX279GAL4; lane c: plasmid YpGX275GAL4; lane d: plasmid YpGX283GAL4; lane e: plasmid YpGX284GAL4; lane f: molecular weight markers.

YpGX279 was digested with enzymes NotI and BamHI and the small fragment encoding 20-decapeptide repeats was gel purified. YpGX275 was digested with NotI and BamHI and the large vector fragment carrying the yeast expression module and replication sequences was gel purified. These two fragment were then ligated and E. coli was transformed the resulting vector YpGX284 was isolated. The GAL4 gene was added to YpGX284 as a HindIII site. The bioadhesive precursor analog protein encoded by YpGX284GAL4 is PH05
signal-asp-ile-lys-ser-met-ala-ala-[(ala-lys-pro-ser-tyr-pro-pro-thr-tyr-lys)₅-thr-pro-ala]₄-ser-met-pro-ala-gly-arg-leu To determine if the S. cerevisiae strains produced bioadhesive precursor analog protein of the expected molecular weight at high levels, yeast strain D8 transformed with expression vectors YpGX275GAL4, YpGX277GAL4, YpGX279GAL4, YpGX283GAL4, and YpGX284GAL4 were first grown on YNBD solid medium (0.7% yeast nitrogen base, 10% glucose, 2% agar) and were then inoculated into 10 ml YPD (1% yeast extract, 2% peptone, 2% glucose) so that the initial A600 reading was 0.1 and were then grown at 28° C. with shaking for 17-24 hours. The cells were harvested and washed with 10 ml YPGal (1% yeast extract, 2% peptone, 2% galactose) and resuspended in an equal volume of YPGal and induced for 6–28 hours. One ml of each culture was harvested and washed with $T_{25}$ $E_{125}$ pH 8.4 buffer (25mM Tris-HCl, 125 mM EDTA, pH 8.4). The cells were then harvested, resuspended in 100 $T_{25}$ $E_{125}$ buffer, and broken by vortexing in the presence of glass beads. Following the addition of 200 ul $T_{25}$ $E_{125}$, the cell lysate was removed from the glass beads and cell debris was pelleted in a microfuge for five minutes. The insoluble pellet was resuspended in 200 ul sample buffer (Laemmli, U.K. 1970, Nature 227:680–685) and boiled for five minutes. A 25 ul aliquot was examined on a 10% SDS-polyacrylamide gel and stained with Coomassie blue. The results of this analysis (FIG. 12) showed that bioadhesive precursor analog proteins of the appropriate molecular weights were produced by the yeast strains at levels of approximately 5 percent of the total cell protein.

To grow yeast strain D8(YpGX284GAL4) in a fermentor, cells were inoculated from an agar plate to 50 ml of the Inoculation medium shown below and grown at 30° C. for 24–36 hours. At an optical density (A600) of 4.0 to 6.0, 5–10 ml of culture were transferred to 500 ml of the Inoculation medium and grown for 24–36 hours at 30° C. At an optical density of 4.0–6.0, the culture broth was transferred to a fermentor charged with 9.4 liters of the Production medium.

| Inoculation medium: | |
|---|---|
| Yeast nitrogen base (Difco) | 0.67 g/L |
| Glucose | 100 g/L |
| KH₂PO₄ | 5 g/L |
| MgSO₄.7H₂O | 5 g/L |
| pH 4.5 | |
| Production medium: | |
| Yeast extract | 15 g/L |
| Peptone | 15 |
| *Glucose | 20 |
| KH₂PO₄ | 5 |
| MgSO₄.7H₂O | 5 |
| *Galactose | 10 |
| Inositol | 0.10 |
| *Thiamine | 0.001 |
| Sag 4130 | 0.25 mL/L |

*Add post autoclaving

The cells were propagated in the Production medium for approximately 40–45 hours at which time an optical density of about 50–55 was attained. The fermentation conditions were:

| | |
|---|---|
| Temperature | 32° C. |
| Aeration | 1 VVM |
| Agitation | 800 RPM |
| pH | 4.5 ± 0.1 |
| pH titrants | H3PO4, 10% |
| | NaOH, 10% |

The cells were then collected by centrifugation and resuspended in lysis buffer.

EXAMPLE 7

Synthesis, Cloning and Expression in *E. coli* of Sequences Encoding Bioadhesive Precursor Protein Analogs Containing Several Different Decapeptides and Hexapeptides Based on the various decapeptide and hexapeptide sequences observed in the *M. edulis* bioadhesive protein cDNA clones (U.S. patent application, Ser. No. 933,945), synthetic genes were constructed that encoded bioadhesive precursor protein analogs with a greater diversity in the amino acid sequence of the polypeptide repeats present.

A. Assembly of pGX2385 and pGX2386. The oligonucleotides listed below were designed to code for one hexapeptide and four different decapeptides found in *M. edulis* polyphenolic protein (based on cDNA sequence data in FIGS. 13-16). The codon choices were made based on those codons predominately used by the yeast *S. cerevisiae* in genes that are expressed at high levels.

In addition to these coding sequences, 5' and 3' linkers were designed to allow production of in-frame fusions with the trpB gene of pGX2346 or related plasmids. The sequences of the linkers are:

```
Oligo #
                        met ala ala ala tyr lys
 2201  5' linker  CG ATG GCG GCC GCT
 2200                 TAC CGC CGG CGA ATG TTC
                  ClaI        NotI tyr lys gly thr ser met
 2198  3' linker  TAC AAG GGT ACC AGC ATG
 2199                         CCA TGG TC
                              Asp718      SphI
```

The 5' linker contains a NotI recognition site and the 3' linker contains a Asp718 recognition site. Therefore, if one batch of plasmid is digested with NotI and a second batch is digested with Asp178 followed by DNA polymerase I treatment to fill in the 5' overhangs, the DNAs can be ligated to create a new doubled gene as shown below:

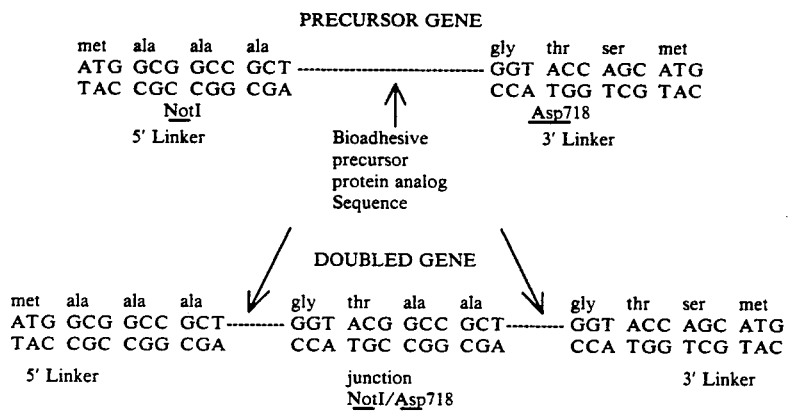

This process can be repeated several times with ever increasing gene size to give exponential size increases and very large synthetic genes. Restriction sites and codons were chosen within the 5' and 3' linkers so that the in-frame fusion can be produced, but also so that the amino acids encoded by the linkers and junction sequences are mostly ones normally found in the natural bioadhesive protein decapeptide repeats. The only exception is the glycine codon of the 3' linker which also carries over to the junction sequence.

```
Oligo #                 ala lys pro thr tyr lys                    hexapeptide
 2197           TAC AAG GCT AAG CCA ACT
 2196                   CGA TTC GGT TGA ATG TTC pro lys pro ser tyr pro pro thr tyr lys          decapeptide
 2194   TAC AAG CCA AAG CCA TCT TAC CCA CCA ACT                         1
 2195           GGT TTC GGT AGA ATG GGT GGT TGA ATG TTC pro lys ile thr tyr pro ser thr tyr lys          decapeptide
 2193   TAC AAG CCA AAG ATT ACT TAC CCA TCT ACT                         2
 2192           GGT TTC TAA TGA ATG GGT AGA TGA ATG TTC ile lys pro thr tyr pro ser thr tyr lys          decapeptide
 2191   TAC AAG ATT AAG CCA ACT TAC CCA TCT ACT                         3
 2190           TAA TTC GGT TGA ATG GGT AGA TGA ATG TTC ala lys pro thr tyr pro ser thr tyr lys          decapeptide
 2189   TAC AAG GCT AAG CCA ACT TAC CCA TCT ACT                         4
 2188           CGA TTC GGT TGA ATG GGT AGA TGA ATG TTC
```

The oligonucleotides were synthesized on an Applied Biosystems automated DNA synthesizer using phosphoramidite chemistry. Each oligonucleotide was dissolved in H₂O at a concentration of 1.0 A 260 unit/ml. All the oligonucleotides except 2200 and 2199 were phosphorylated with T4 polynucleotide kinase. Twenty ul of a 1.0 O.D./ml solution (0.66 ug) of the oligonucleotides was kinased in a 60 ul volume at 37° C. for 1.5 hours. The reactions were boiled for two minutes then mixed with their complement, i.e., 2196 with 2197, 2194 with 2195, 2192 with 2193, 2190 with 2191, 2188 with 2189. The phosphorylated oligonucleotide 2201 was mixed with an equal amount of non-phosphorylated 2200 to make the 5' linker and the phosphorylated 2198 was mixed with an equal amount of non-phosphorylated 2199 to make the 3' linker. After mixing, the samples were heated to boiling, allowed to cool slowly to 20° C. and then placed on ice to allow annealing.

Ten micrograms of pGX2287 DNA (NRRL-B15788) was digested in a 100 ul volume with 18 units of ClaI (Boehringer-Mannheim). The 10 ug of ClaI cut pGX2287 DNA was ligated in a 40 ul volume reaction with 30 ul of the 5' linker solution for 4.5 hours at 15° C. The ligation solution was diluted to 1 ml then concentrated to 50 ul with a Centricon 30 filter (Amicon Corp.). The dilution and reconcentration was repeated two more times to remove non-ligated linkers. The DNA was phenol-chloroform extracted and ethanol precipitated and dissolved in 40 ul H₂O.

A ligation to insert a bioadhesive precursor protein analog gene into pGX2287 with the 5' linker was performed as follows. Approximately 2.5 ug of the modified pGX2287 DNA was ligated in a 40 ul reaction volume reaction containing 4 ul of each of the decapeptide coding oligonucleotide solutions (2194 and 2195, 2192 and 2193, 2190 and 2191, 2188 and 2189) and 2 ul of the hexapeptide coding oligonucleotide solution (2196 and 2197). Two approaches were taken for the addition of 3' linker oligonucleotide (2198 and 2199). Either a smaller amount was added to the ligation (1-3 ul) right from the start, or the ligation was allowed to proceed without 3' linker for 15 minutes to an hour. The 3' linker was then added in excess (5-10 ul). Since the SpHI end of the 3' linker was not phosphorylated, the addition of the 3' linker to the gene terminates further increase in size. The oligonucleotide ligation reactions were diluted to a volume of 100 or 150 ul in SphI digestion buffer and cut with SpHI The digests were extracted with phenol-chloroform then ethanol precipitated including the addition of 10 ug tRNA. Finally, half of the SphI cut ligation mixture (1.25 ug of original pGX2287 vector) was ligated at low concentration in a volume of 150 ul to allow circularization. The final ligations were used to transform E. coli GX3105 and plated on minimal salts media with 0.4% acid hydrolyzed casamino acids (Difco) that has no tryptophan, 0.4% glucose, ug/ml nicotinic acid, 1 ug/ml biotin, and 100 ug/ml ampicillin. The resulting transformants with plasmids that are trp+ Ap+ were grown and the plasmids were analyzed. Two plasmids that were characterized, (pGX2385 and pGX2386) contain bioadhesive precursor protein inserts of approximately 280 base pairs and 200 base pairs, respectively. The DNA sequence and protein translation of the inserts in pGX2385 and pGX2386 are shown in FIGS. 17 and 18 respectively. Examination of the DNA sequence of the synthetic genes in pGX2385 and pGX2386 demonstrated that these genes contain the hexapeptide and three of the four decapeptide coding sequences described above. Only decapeptide 4 (oligo 2189 and 2188) is not represented in these two examples. Transformants containing pGX2385 and pGX2386 produced protein that reacted with both anti-chymosin antibody and the anti-bioadhesive precursor protein analog antibody described in Example 3.

B. Expansion of the Coding Sequences in pGX2385 and pGX2386. The bioadhesive precursor protein analog coding sequences contained in pGX2385 and pGX2386 can be expanded by the method described in Example 4 or by a related method that gives a junction sequence which itself codes for a decapeptide. For this latter method the oligonucleotides shown below were synthesized that together have single stranded ends complementary to the Asp718 and NotI generated ends in the 3' and 5' linkers used in the primary gene assembly described above.

```
             thr   lys   ser   tyr   pro
#2220    GT ACT   AAG   TCT   TAC   CC
#2221        A    TTC   AGA   ATG   GGC   CGG
```

The linker was designed such that after ligation to join two synthetic genes, the linker creates the decapeptide coding sequence shown below between the last decapeptide coding repeat of one original gene and the first decapeptide coding repeat of the second original gene.

```
adjacent                                                                              adjacent
repeat                                                                                repeat
...tyr   lys   gly   thr   lys   ser   tyr   pro   ala   ala   tyr   lys   pro   lys   pro ...
...TAC   AAG   G GT  AC T  AAG   TCT   TAC   CC G  GCC   GCT   TAC   AAG   CCA   AAG   CCA...
...ATG   TTC   C CA  TG A  TTC   AGA   ATG   GG C  CGG   CGA   ATG   TTC   GGT   TTC   GGT...

Asp718 end                    NotI end in
         in 3' linker                  5' linker
         sequence                      sequence
```

This new decapeptide, coded by the new junction, is not exactly the same as any decapeptide repeat found in the cDNA clones, but it is closely related and contains amino acids normally found in M. edulis polyphenolic protein repeats (with the exception of the glycine). Using similar methods it is possible to design other related linker sequences.

Ten micrograms of pGX2385 DNA was cut with Asp718 (Boehringer-Mannheim) and ten micrograms of pGX2386 DNA was digested with NotI (New England Biolabs), both in a volume of 100 ul. The DNAs were extracted with phenol-chloroform, precipitated, then dissolved in 10 ul of water. Half of the Asp718 cut pGX2385 was ligated in a 60 ul volume with annealed oligos 2221 and 2220 where 2220 had been previously phosphorylated with ATP and T4 polynucleotide kinase. Approximately 1 ng of linker was added. After ligation, non-bound linkers were removed by concentrating and rinsing the DNA in a Centricon 30 (Amicon) filtration unit. After precipitation, the DNA was ligated in a 20 ul volume with 5 ul (5 ug) of the NotI cut pGX2386 DNA. After ligation, the mixture was diluted to 100 ul and digested with PvuI. One fourth of the PvuI cut DNA was finally ligated in a volume of 150 ul to promote circle formation of the plasmid. The final ligation mixture was used to transform GX3015 cells. One transformant contained a plasmid with the expected structure which named pGX2393. The DNA sequence of the pGX2393 is shown in FIG. 19.

The bioadhesive precursor protein analog gene in pGX2393 was doubled in size by taking advantage of the unique Asp718 site 3' of the gene, the unique NotI site 5' of the gene, and the unique MluI site located 3013 bases upstream of the NotI site. pGX2393 DNA was restricted with NotI and MluI, and the larger fragments (5.2 kb) was gel-purified. Plasmid pGX2393 DNA was also cut with Asp718 and MluI and the smaller fragment (3.4 kb) was gel-purified. The two fragments were ligated together with oligomers 2220 and 2221 (nonphosphorylated) which had previously been annealed. *E. coli* GX1210 (NRRL B-15800) was transformed with the ligation mix. The resulting plasmid YpGX288 should encode 27 decapeptides and six hexapeptides.

Two further doublings of the bioadhesive precursor protein analog gene were accomplished analogously, gel-purifying fragments of the appropriate sizes and ligating them together with the annealed oligomers. This resulted in YpGX289 which should encode 55 decapeptides and 12 hexapeptides, and YpGX290 which should encode 111 decapeptides and 24 hexapeptides. Although DNA sequencing of these plasmids was not performed, *E. coli* cells with YpGX288 and YpGX289 were observed to produce proteins reactive with anti-decapeptide antibody of Example 3 in Western blot experiments. The proteins were of the molecular weight expected for polyphenolic-chymosin fusion proteins with 306 amino acids and 622 amino acids, respectively in the bioadhesive precursor protein analog segment.

EXAMPLE 8

Expression in *S. cerevisiae* of Sequences Encoding Bioadhesive Precursor Protein Analogs Containing Several Different Decapeptides and Hexapeptides To insert the bioadhesive precursor analog protein coding sequence assembled in Example 7 into the yeast expression module present in YpGX265GAL4 the following method was used. M13 vector MGX451 was assembled by inserting the bioadhesive precursor analog coding sequence, yeast promoter and PH05 signal encoding sequence from YpGX277GAL4 (Example 6) as a HindIII-SphI restriction fragment into HindIII and SphI digested M13mp18. MGX451 was digested with NotI and SphI and the large fragment was gel purified. YpGX288 (see Example 7) was digested with NotI and SpHI and the small fragment carrying the bioadhesive precursor protein analog coding sequence was gel purified. The two purified fragments were ligated and *E. coli* was transformed. The desired transformant, having the heterogenous bioadhesive precursor analog coding sequence inserted in the yeast expression module was called MGX456. MGX456 was digested with NotI and and the small vector fragment was gel purified. YpGX284 was digested with NotI and BamHI and the large vector fragment was gel purified. These two fragments were then ligated and transformed into *E. coli*. The resulting expression vector was designated YpGX291. The GAL4 gene was then added to the unique HindIII site of YpGX291 to generate YpGX291GAL4.

In the same manner, the bioadhesive precursor protein analog coding sequence from plasmid YpGX290 (Example 7) was transferred to a yeast expression vector to generate YpGX297GAL4. During this genetic construction a deletion occurred within the bioadhesive precursor analog protein coding sequence resulting in a sequence encoding a protein of 100,000 rather than 138,000 daltons.

Yeast strain D8 was transformed with YpGX291GAL4 and YpGX297GAL4 and the translation products were analyzed as in Example 6. This analysis showed that strain D8 (YpGX291GAL4) produced a bioadhesive precursor protein analog of about 34,000 daltons as expected and this protein composed about 5% of the total yeast cell protein. The same analysis showed that strain D8(YpGX297GAL4) produced a bioadhesive precursor analog protein of about 100,000 daltons and this protein composed about 1-2% of the total yeast cell protein. The size of the bioadhesive precursor protein produced by strain D8 (YpGX297GAL4) was smaller than predicted by the coding sequence present in *E. coli* vector YpGX290 (138,000 daltons) reflecting the deletion event that occurred during construction of the yeast expression vector.

EXAMPLE 9

Purification of Bioadhesive Precursor Protein Analogs

*E. coli* GX3015 cells containing one of the plasmids described in Example 4 or 7 (32 g wet weight) are suspended in 20 ml 20 mM Tris-HCl, 2 mM EDTA (pH 7.5), 1 mM phenylmethylsulfonyl fluoride, 25 mM iodoacetic acid, and thoroughly disrupted by passage through a French press followed by sonication. The cell debris and inclusion bodies containing bioadhesive precursor protein are pelleted by centrifugation at 27,500 g for 30 minutes at 4° C. The pellet is extensively washed by suspension in 10 mM Tris-HCl, 1 mM EDTA (pH 7.5) and centrifugation. Washing is continued until the supernatant is clear. The pellet is then dissolved in 15 ml of 6 M guanidine hydrochloride, 5% beta-mercaptoethanol, 25 mM iodoacetic acid, and centrifuged at 30,000 x g for 30 minutes at 4° C. The supernatant is dialyzed against 4 liters of 0.2 mM EDTA, 10 mM iodoacetic acid, with 3 changes which results in protein precipitation. The precipitate containing about 0.5 g of protein is dissolved in 40 ml of 70% formic acid. Cyanogen bromide (1.3 g) is added and the solution is allowed to react overnight at room temperature. After rotary evaporation, the residue is extracted with 20 ml water (pH 4.0 from residual formic acid). The pH of the water-soluble fraction is adjusted to pH 7.0 with 5 N KOH resulting in some precipitate formation. The supernatant is then applied to a CM cellulose or S-Sepharose column (2.5×26 cm) equilibrated with 50 mM potassium phosphate (pH 7.5). After the column is washed for 14 hours with 50 mM potassium phosphate, the bioadhesive precursor protein is eluted with either a salt gradient (0 to 0.5 M KCl) or a pH change (pH 8 to pH 10) in the buffer. The fractions are assayed by measurement of absorbance at 280 nm and by SDS polyacrylamide gel electrophoresis using both Coomassie blue protein stain and the Western blot assay with specific antibodies (Example 3). The fractions containing the bioadhesive precursor protein analog are pooled and dialyzed overnight twice against 2 liters of deionized water. The resultant suspension is lyophilized and 1 mg of purified material is obtained. Material could be further purified, if necessary, using Sephadex G-75 column chromatography with 0.3 M ammonium acetate pH 4.0. Bioadhesive precursor protein eluting in the first protein peak is dialyzed against water and lyophilized for recovery as a salt-free powder.

The purified protein is hydrolyzed in 6 M constant boiling HCl with phenol crystals in vacuo at 105° C. for 24 hours. The amino acids in the acid hydrolysate are identified as O-phthaldehyde (OPA) derivatives which are separated on C18 reverse-phase HPLC column (Fleury, M. O. and D. V. Ashley, *Anal. Biochem.*, 133:330-335 (1983)). The amino acid composition is used to verify purity since only a subset of amino acids is present in bioadhesive precursor protein.

EXAMPLE 10

Scaled-up Method for Bioadhesive Precursor Protein Analog Purification

*E. coli* cells or yeast cells from a 180 liter fermentation were centrifuged in a Westphalia centrifuge, washed with saline and resuspended as 30% solids in 10 mM EDTA, 10 mM phenylmethylsulfonyl fluoride (PMSF), 10 mM iodoacetic acid (IAA) pH 8.0 before breaking by a Manton-Gaulin homogenizer. Bioadhesive precursor protein analog present in an insoluble fraction was collected with the cell debris by Westphalia centrifugation. The centrifugation pellet was resuspended to 20% solids in acetic or formic acid at pH 2.2 to 2.5 and mixed for several hours to solubilize the bioadhesive precursor protein analog. The extract was centrifuged or filtered to remove solids and the clear filtrate solution was then adjusted to pH 4 with 5 N KOH in the presence of 10 mM EDTA, 10 mM IAA and 1.0 mM PMSF. Impurities were removed as a precipitate by filtration or centrifugation. The bioadhesive precursor protein analog in the clear supernatant was then concentrated by ultrafiltration (10,000 M.W. cutoff membrane) and subsequently lyophilized. After the residue (approximately 50-100 g) was dissolved in 1.2 liter of 70% formic acid, cyanogen bromide (100 q) was added and the solution was stirred for 24 hours at room temperature. The reaction mixture was then dried by rotary evaporation and the residue was dissolved in 50-100 ml 6 M guanidine hydrochloride at pH 8.0 and centrifuged at 30,000 g for 20 minutes at 4° C. The supernatant was chromatographed on a Sephacryl S-300 column equilibrated with the same solution. The fractions containing bioadhesive precursor protein were collected, adjusted to pH 4.0 with acetic acid, dialyzed against water and lyophilized to recover as a salt-free powder.

EXAMPLE 11

Hydroxylation of Bioadhesive Precursor Protein

Since tyrosinase has been known to catalyze the hydroxylation of tyrosine and oxidation of DOPA (Ito et al., *Biochem.*, 222:407-411 (1984); Marumo and Waite, *Biochem. Biophys. Acta*, 892:98-103 (1986)), mushroom tyrosinase or *Streotomyces antibioticus* tyrosinase can be used to enzymatically modify the homogenous *E. coli* or yeast-produced bioadhesive precursor protein analog. To a 1 ml mixture containing a 2 mg protein, 25 umole ascorbic acid and 0.05 M sodium phosphate between pH 5 to 7.5, 0.1 mg mushroom tyrosinase (Sigma Chemical Co.) is added. The mixture is allowed to react at room temperature for 3 hours. The kinetics of the hydroxylation process can be monitored by the colorimetric assay for DOPA and DOPA-derived quinone (Waite, J. H. and M. L. Tanzer, *Anal. Biochem.*, 111:131-136 (1981)). Amino acid analysis is performed after acid hydrolysis as above (Example 9). After correcting for loss during the recovery process, amino acid analysis indicates approximately 40% of the tyrosine residues are converted to DOPA.

After hydroxylation, the pH of the solution is adjusted to 4 with acetic acid and the solution is dialyzed against 100 volumes of 5% acetic acid. The samples are rotatory-evaporated to reduce the volume. The tyrosinase is removed either by using a LH-Sephadex 60 column, which is eluted with 0.2 M acetic acid, or using a membrane filtration method (Amicon PM30, cut off of 30,000 M.W.).

An alternative purification scheme after hydroxylation is described below. After CNBr cleavage, the supernatant obtained at pH 7.0 (see Example 9) is acidified to between pH 5 and 7 in the presence of ascorbic acid or tropolone (Kahn, V. and A. Andrawis, *Phytochemistry*, 24:905-908 (1985)). Hydroxylation is started by the addition of tyrosinase. At the end of the reaction, the sample is purified by an SE Sephadex column. The fractions containing DOPA are pooled, dialyzed against 2.5% acetic acid and lyophilized. The purity of the hydroxylated protein is established by acid-urea polyacrylamide gel electrophoresis (Panyium S. and R. Chalkley, *Arch. Biochem. Biophys.*, 130:337-346 (1969)) and amino acid analysis.

The DOPA-containing bioadhesive protein analog is then ready for formulation as an adhesive.

EXAMPLE 12

Use of Bioadhesive Protein Analogs as Primers for Conventional Adhesives

Surfaces such as metals or plastics are frequently given a pretreatment such as oxidation with acid, flame treatment or plasma bombardment to improve the ability of the surface to "wet" or interact with the adhesive.

Microbially produced and hydroxylated bioadhesive protein analog coated onto a surface can be used as a pretreatment or priming substance for conventional adhesives. An example of the use of a bioadhesive protein analog as a primer treatment for bonding two pieces of aluminum is given below.

Hydroxylated bioadhesive protein analog prepared as in Example 11 is dissolved in degassed water (optimally at pH 7.0 to 8.0) at a concentration of 10-400 mg/ml (10-40% w/v). The solution is maintained under nitrogen to prevent premature oxidation of DOPA residues to quinones and curing of the adhesive primer.

The bioadhesive protein analog solution is sprayed or painted to uniformly moisten an oil-free aluminum surface in a normal air environment. The surface is then dried in a low-humidity environment. A brown or tan color may develop indicating quinone oxidation and chemical cross-linking. The primed surfaces to be bonded are then joined using standard materials such as epoxy glue.

As an alternative to speed bioadhesive protein analog curing and eliminate the prehydroxylation step (see Example 11), an enzyme such as mushroom tyrosinase (Ito et al., *Biochemistry*, 222:407-411 (1984)) or Streotomyces tyrosinase (Lerch and Ettlinger, *Eur. J. Biochem.*, 31:427-437 (1972)) is mixed with the non-hydroxylated protein (Example 10) immediately prior to application (for example, in the nozzle of a spray applicator) at a concentration of 0.01 to 1.0 mg/ml solution. The enzyme under these conditions effects oxidation all the way from tyrosine to the reactive quinone species.

Blends of bioadhesive protein analogs with other polymers (as outlined in adhesive examples given below) are also used as primers for other adhesives.

EXAMPLE 13

Use of Bioadhesive Protein Analogs

The hydroxylated bioadhesive protein prepared as in Example 11 is dissolved at a concentration of 30–700 mg/ml (3–70% solids) in water (or a physiological salt solution for medical applications) adjusted to pH 6.0 with dilute acids.

Immediately prior to application to a surface, a basic solution (approximately 1/50 volume) is added to increase the pH to 8.0. An enzyme such as mussel catechol oxidase (Waite, J. H., *J. Mar. Biol. Assoc.*. 65:359–371 (1985)) can also be added (final concentration 0.01–1 mg/ml) in place of or in addition to base solution immediately prior to application to accelerate the oxidation of DOPA residues to quinones to yield more rapid curing. Mixing of components immediately prior to application can occur, for example, in a spray head of a Duploject ® syringe as has been described for fibrin sealant (Redl, H. and G. Schlag, *Facial Plastic Surgery*, 2:315–321 (1985)). Alternative enzymes such as mushroom tyrosinase (Ito et al., Biochemistry. 222:407–411 (1984)) or Streotomyces tyrosinase (Learch and Ettlinger, *Eur. J. Biochem.* 31:427–437 (1972)) are also used. With tyrosinase, the bioadhesive precursor protein need not be previously hydroxylated and thus the material without prior hydroxylation described in Example 10 may be used. In order for oxidation of DOPA residues to quinones to take place and subsequent curing (either with or without enzymes), there must be dissolved oxygen present in the bioadhesive protein solution.

EXAMPLE 14

Composites of Bioadhesive Protein Analog with Other Protein Polymers

In order to moderate and improve the properties of the mussel polyphenolic protein adhesive, blends with other polymers are used. The bioadhesive protein is naturally associated with collagen in the byssal threads of the mussels. Collagen is one natural polymer that can be used to increase the cohesive strength of phenolic protein composites. Acid-soluble collagen (Gallop, P. M. and S. Seifter, *Methods Enzymol.*, VI:635–641 (163) is dissolved in dilute acid solution at 10–70% (w/v). The collagen is mixed with the bioadhesive protein mixtures as described in Example 13 in ratios having from 1% to 50% of the solids comprising bioadhesive protein with total solids ranging from 10 to 70%. Higher percentages of bioadhesive protein yield more highly cross-linked rigid composites than those with lower percentages of bioadhesive protein. Alkaline solution may be used to neutralize the mixture immediately prior to application. This allows more rapid oxidation and cross-linking (curing) of the mixture. Also, at neutral pH, the collagen will crystallize, providing added cohesive strength.

Alternatively, the bioadhesive protein is used in combination with preformed sheets of collagen. This method is analogous to the use of reinforcing steel in cement or graphite fiber in epoxy composites. Collagen sheets such as the commercially available collastat (a Helitrex product distributed by American Home Products Corporation) or other similar products are sprayed or soaked in bioadhesive protein activated as described above in Example 13, then applied to the surface to be bonded.

In a similar manner, other types of insoluble or crystalline protein sheets can be used as reinforcement for adhesive protein. For example, silk cloth, or sheets formed from solubilized and reprecipitated alpha-keratose from wool keratin fibers (J. De Bersagbes, *Curr. Probl. Dermatol.*, 6:34–86 (1976)), or polymerized fibrin clot formed from purified fibrinogen, thrombin and Factor VIII (Redl, H. and G. Schlag, *Facial Plastic Surgery*, 2:315–321 (1985)) are used. For medical applications, the use of sheets of fibrin may have the additional benefit of helping to promote wound healing (Redl and Schlag, supra).

EXAMPLE 15

Composites of Bioadhesive Protein with Carbohydrate Polymers

Chitosan is dissolved in 1% acetic acid to a concentration of 30–150 mg/ml (3–15% w/v). The chitosan solution with a final pH of approximately 6.0 is blended with an hydroxylated bioadhesive protein analog prepared as described in Example 11. Blends typically have bioadhesive protein concentrations between 2 and 30% and chitosan concentrations between 1 and 7%. At pH 6.0 where the chitosan is still soluble tyrosinase addition catalyzes the formation of reactive DOPA-derived quinones and cross-linking. Increasing the pH to 8.0 prior to application results in the immediate precipitation of chitosan out of solution which in some cases may not be desirable.

What is claimed is:

1. A method for producing a bioadhesive precursor protein analog said method comprising:

(A) constructing a DNA sequence comprising DNA encoding a synthetic protein, said synthetic protein comprising the amino acid sequence of a bioadhesive precursor protein analog, said bioadhesive precursor protein analog being about 50–1500 amino acids in size and consisting essentially of tandemly liked peptide units, wherein said units may be the same or different and wherein each unit has the formula X-tyrosine-lysine, adjacent units being separated by a junction sequence of 0–10 amino acids, wherein n=4–8, X is any amino acid, and wherein each unit contains one to four prolines and also one to four amino acids selected from the group consisting of serine and threonine, and at least one unit is selected from the group consisting of:

a. P K P S Y P P S Y K
b. P K T T Y P P T Y K
c. P K I S Y P P T Y K
d. A K P S Y P A T Y K
e. V K P T Y K
f. S K P T Y K
g. P K P S Y P P T Y K
h. S K S I Y P S S Y K
i. P K K T Y P P T Y K
j. P K L T Y P P T Y K k. P K I T Y P S T Y K
l. L K P S Y P P T Y K
m. A K P T Y P P S Y K
n. K K I S Y P S S Y K
o. A K T S Y P P A Y K
p. A K P T Y P S T Y K
q. A K P T N P S T Y K
r. A K P S Y P S T Y K
s. A K S S Y P P T Y K
t. A K P T Y K
u. A K T N Y P P V Y K
v. P K M T Y P P T Y K
w. P K I T Y P P T Y K
x. P K A S Y P P T Y K
y. T K K T Y P P T Y K
z. A K P S Y P P T Y K
a'. A K P T Y P P T Y K
b'. A K P S Y P P S Y K (B) inserting the DNA of part (a) into a recombinant vector to provide an expression vector comprising
    (i) said DNA sequence; and
    (ii) promoter and transcription initiation signals, operably linked to said DNA sequence, said promoter and said transcription initiation signals being capable of effecting expression of said bioadhesive precursor protein analog encoded by said DNA sequence in a host cell;
(C) transforming said host with said expression vector;
(D) expressing said bioadhesive precursor protein analog; and
(E) recovering said bioadhesive precursor protein analog.

2. A method for producing a bioadhesive precursor protein analog said method comprising:
(A) culturing a host which has been transformed with a recombinant vector comprising;
    (i) a DNA sequence encoding a synthetic protein, said synthetic protein comprising the amino acid sequence of a bioadhesive precursor protein analog, said bioadhesive precursor protein analog being about 50-1500 amino acids in size and consisting essentially of tandemly linked peptide units, wherein said units may be the same or different and wherein each unit has the formula $X_n$-tyrosine-lysine, adjacent units being separated by a junction sequence of 0-10 amino acids, wherein n=4-8, X is any amino acid, and wherein each unit contains one to four prolines and also one to four amino acids selected from the group consisting of serine and threonine, and at elast one unit is selected from the group consisting of:
a. P K P S Y P P S Y K
b. P K T T Y P P T Y K
c. P K I S Y P P T Y K
d. A K P S Y P A T Y K
e. V K P T Y K
f. S K P T Y K
g. P K P S Y P P T Y K
h. S K S I Y P S S Y K
i. P K K T Y P P T Y K
j. P K L T Y P P T Y K
k. P K I T Y P S T Y K
l. L K P S Y P P T Y K
m. A K P T Y P P S Y K
n. K K I S Y P S S Y K
o. A K T S Y P P A Y K
p. A K P T Y P S T Y K
q. A K P T N P S T Y K
r. A K P S Y P S T Y K
s. A K S S Y P P T Y K
t. A K P T Y K
u. A K T N Y P P V Y K
v. P K M T Y P P T Y K
w. P K I T Y P P T Y K
x. P K A S Y P P T Y K
y. T K K T Y P P T Y K
z. A K P S Y P P T Y K
a'. A K P T Y P P T Y K
b'. A K P S Y P P S Y K and
    (ii) promoter and transcription initiation signals, operably linked to said DNA sequence, said promoter and said transcription initiation signals being capable of effecting expression of said bioadhesive precursor protein analog in a host;
(B) expressing said bioadhesive precursor protein analog; and
(C) recovering said bioadhesive precursor protein analog.

3. The method of any of claims 1 or 2, wherein the composition of said bioadhesive precursor protein analog is 20-40% proline, 10-40% lysine, 10-40% tyrosine, and 0-40% amino acid residues other than proline, lysine, and tyrosine.

4. The method of any of claim 1 or 2, wherein said bioadhesive precursor protein analog contains 5-135 peptides units.

5. The method of any of claims 1 or 2, wherein said junction sequence is 0-3 amino acids.

6. The method of any of claims 1 or 2, wherein said bioadhesive precursor protein analog contains the amino acid sequence of the bioadhesive precursor protein analog of FIG. 9.

7. The method of any of claims 1 or 2, wherein said bioadhesive precursor protein analog contains the amino acid sequence of the bioadhesive precursor protein analog of FIG. 17.

8. The method of any of claims 1 or 2, wherein said bioadhesive precursor protein analog contains the amino acid sequence of the bioadhesive precursor protein analog of FIG. 18.

9. The method of any of claims 1 or 2, wherein said bioadhesive precursor protein analog contains the amino acid sequence of the bioadhesive precursor protein analog of FIG. 19.

10. The method of any one of claim 1 or 2, wherein said synthetic protein comprises a secretion signal peptide operably linked to said amino acid sequence of said bioadhesive precursor protein analog.

11. The method of any one of claims 1 or 2 wherein said synthetic protein is a fusion protein, wherein said fusion protein comprises said amino acid sequence of said bioadhesive precursor protein analog linked in-frame, at its 5' end, to at least five amino acids of a proximal N-terminal sequence of a microbial protein that is in the genome of said host cell, normally operably linked to the promoter being used to express said DNA encoding said synthetic protein.

12. The method of any one of claims 1 or 2 wherein said DNA sequence encoding said bioadhesive precursor protein analog utilizes preferred host codons.

13. A recombinant vector comprising a DNA sequence encoding a synthetic protein, said synthetic protein comprising the amino acid sequence of a bioadhesive precursor protein analog, said bioadhesive precursor protein analog being about 50-1500 amino acids in size and consisting essentially of tandemly linked peptide units, wherein said units may be the same or different and wherein each unit has the formula $X_n$-tyrosine-lysine, adjacent units being separated by a junction sequence of 0-10 amino acids, wherein n=4-8, X is any amino acid, and wherein each unit contains one to four prolines and also one to four amino acids selected from the group consisting of serine and threonine, and at least one units is selected from the group consisting of:

a. P K P S Y P P S Y K
b. P K T T Y P P T Y K
c. P K I S Y P P T Y K
d. A K P S Y P A T Y K
e. V K P T Y K
f. S K P T Y K
g. P K P S Y P P T Y K
h. S K S I Y P S S Y K
i. P K K T Y P P T Y K
j. P K L T Y P P T Y K
k. P K I T Y P S T Y K
l. L K P S Y P P T Y K
m. A K P T Y P P S Y K
n. K K I S Y P S S Y K
o. A K T S Y P P A Y K
p. A K P T Y P S T Y K
q. A K P T N P S T Y K
r. A K P S Y P S T Y K
s. A K S S Y P P T Y K
t. A K P T Y K
u. A K T N Y P P V Y K
v. P K M T Y P P T Y K
w. P K I T Y P P T Y K
x. P K A S Y P P T Y K
y. T K K T Y P P T Y K
z. A K P S Y P P T Y K
a'. A K P T Y P P T Y K
b'. A K P S Y P P S Y K.

14. The vector of claim 13, wherein the composition of said bioadhesive precursor protein analog is 20-40% proline, 10-40% lysine, 10-40% tyrosine, and 0-40% amino acid residues other than proline, lysine, and tyrosine.

15. The vector of claim 13, wherein said bioadhesive precursor protein analog contains 5-135 peptide units.

16. The vector of claim 13, wherein said junction sequence is 0-3 amino acids.

17. The recombinant vector of claim 13, wherein said bioadhesive precursor protein analog contains the amino acid sequence of the bioadhesive precursor protein analog of FIG. 9.

18. The recombinant vector of claim 13, wherein said bioadhesive precursor protein analog contains the amino acid sequence of the bioadhesive precursor protein analog of FIG. 17.

19. The recombinant vector of claim 13, wherein said bioadhesive precursor protein analog contains the amino acid sequence of the bioadhesive precursor protein analog of FIG. 18.

20. The recombinant vector of claim 13, wherein said bioadhesive precursor protein analog contains the amino acid sequence of the bioadhesive precursor protein analog of FIG. 19.

21. The vector of any one of claims 13, 14-16 and 17-20, wherein said synthetic protein comprises a secretion signal peptide operably linked to said amino acid sequence of said bioadhesive precursor protein analog.

22. The vector of any one of claim 13, 14-16 and 17-20, wherein said synthetic protein is a fusion protein, wherein said fusion protein comprises said amino acid sequence of said bioadhesive precursor protein analog linked inframe, at its 5' end, to at least five amino acids of proximal N-terminal sequence of a microbial protein that is, in the genome of said host cell, normally operably linked to the promoter being used to express said DNA encoding said synthetic protein.

23. The vector of any one of claims 13, 14-16 and 17-20, wherein the DNA sequence encoding said bioadhesive precursor protein analog utilizes preferred host codons.

24. A host comprising a recombinant vector, said recombinant vector comprising a DNA sequence encoding a synthetic protein, said synthetic protein comprising the amino acid sequence of a bioadhesive precursor protein analog, said bioadhesive precursor protein analog being about 50-1500 amino acids in size and consisting essentially of tandemly linked peptide units, wherein said units may be the same or different and wherein each unit has the formula $X_n$-tyrosine-lysine, adjacent units being separated by a junction sequence of 0-10 amino acids, wherein n=4-8, X is any amino acid, said wherein each unit contains one to four prolines and also one to four amino acids selected from the group consisting of serine and threonine, and at least one units is selected from the group consisting of:

a. P K P S Y P P S Y K
b. P K T T Y P P T Y K
c. P K I S Y P P T Y K
d. A K P S Y P A T Y K
e. V K P T Y K
f. S K P T Y K
g. P K P S Y P P T Y K
h. S K S I Y P S S Y K
i. P K K T Y P P T Y K
j. P K L T Y P P T Y K
k. P K I T Y P S T Y K
l. L K P S Y P P T Y K
m. A K P T Y P P S Y K
n. K K I S Y P S S Y K
o. A K T S Y P P A Y K
p. A K P T Y P S T Y K
q. A K P T N P S T Y K
r. A K P S Y P S T Y K
s. A K S S Y P P T Y K
t. A K P T Y K
u. A K T N Y P P V Y K
v. P K M T Y P P T Y K
w. P K I T Y P P T Y K
x. P K A S Y P P T Y K
y. T K K T Y P P T Y K
z. A K P S Y P P T Y K
a'. A K P T Y P P T Y K
b'. A K P S Y P P S Y K.

25. The host of claim 24, wherein said host is selected from the group consisting of *E. coli* and *S. cervesiae*.

26. The host of claim 25 wherein said host is *E. coli*.

27. The host of claim 25 wherein said host is *S. cervesiae*.

28. The host of claim 24, wherein the composition of said bioadhesive precursor protein analog is 20-40% proline, 10-40% lysine, 10-40% tyrosine, and 0-40% amino acid residues other than proline, lysine, and tyrosine.

29. The host of claim 24, wherein said bioadhesive precursor protein analog contains 5-135 peptide units.

30. The host of claim 24, wherein said junction sequence is 0-3 amino acids.

31. The host of claim 24, wherein said bioadhesive precursor protein analog contains the amino acid sequence of the bioadhesive precursor protein analog of FIG. 9.

32. The host of claim 24, wherein said bioadhesive precursor protein analog contains the amino acid sequence of the bioadhesive precursor protein analog of FIG. 17.

33. The host of claim 24, wherein said bioadhesive precursor protein analog contains the amino acid sequence of the bioadhesive precursor protein analog of FIG. 18.

34. The host of claim 24, wherein said bioadhesive precursor protein analog contains the amino acid sequence of the bioadhesive precursor protein analog of FIG. 19.

35. The host of any one of claim 24, 25-27, 28-30 and 31-34 wherein said synthetic protein comprises a secretion signal peptide operably linked to said amino acid sequence of said bioadhesive precursor protein analog.

36. The host of any one of claim 24, 25-27, 28-30 and 31-34, wherein said synthetic protein is a fusion protein, wherein said fusion protein comprises said amino acid sequence of said bioadhesive precursor protein analog linked in frame, at its 5' end, to at least five amino acids of a proximal N-terminal sequence of a microbial protein that is, in the genome of said host cell, normally operable linked to the promoter being used to express said DNA encoding said synthetic protein.

37. The host of any one of claims 24, 25-27, 28-30 and 31-34, wherein the DNA sequence encoding said bioadhesive precursor protein analog utilizes preferred host codons.

* * * * *